US007909824B2

(12) United States Patent
Masuda et al.

(10) Patent No.: US 7,909,824 B2
(45) Date of Patent: Mar. 22, 2011

(54) ENERGY ACCESSORY

(75) Inventors: Shinya Masuda, Tokyo (JP); Koh Shimizu, Tokyo (JP); Kenichi Kimura, Tokyo (JP)

(73) Assignee: Olympus Corporation (JP)

( * ) Notice: Subject to any disclaimer, the term of this patent is extended or adjusted under 35 U.S.C. 154(b) by 685 days.

(21) Appl. No.: 11/413,725

(22) Filed: Apr. 28, 2006

(65) Prior Publication Data
US 2006/0259054 A1 Nov. 16, 2006

Related U.S. Application Data

(63) Continuation of application No. PCT/JP2005/010974, filed on Jun. 15, 2005.

(30) Foreign Application Priority Data

Jun. 15, 2004 (JP) ................................. 2004-176780

(51) Int. Cl.
*A61B 18/18* (2006.01)
(52) U.S. Cl. ....................................................... 606/51
(58) Field of Classification Search .............. 606/48, 606/169, 37, 42, 52, 51; 604/22; 600/437; 439/909
See application file for complete search history.

(56) References Cited

U.S. PATENT DOCUMENTS

| | | | | |
|---|---|---|---|---|
| 1,812,608 A | * | 6/1931 | Roberts | 606/42 |
| 4,552,143 A | * | 11/1985 | Lottick | 606/42 |
| 5,403,342 A | * | 4/1995 | Tovey et al. | 606/205 |
| 5,609,573 A | * | 3/1997 | Sandock | 604/22 |
| 5,697,949 A | * | 12/1997 | Giurtino et al. | 606/205 |
| 6,019,758 A | * | 2/2000 | Slater | 606/51 |
| 6,039,752 A | * | 3/2000 | Kimura et al. | 606/205 |
| 6,056,735 A | | 5/2000 | Okada et al. | |
| 6,340,352 B1 | * | 1/2002 | Okada et al. | 601/2 |
| 6,551,315 B2 | * | 4/2003 | Kortenbach et al. | 606/46 |
| 6,558,376 B2 | | 5/2003 | Bishop | 606/27 |
| 6,569,178 B1 | * | 5/2003 | Miyawaki et al. | 606/169 |
| 2002/0183774 A1 | | 12/2002 | Witt et al. | 606/169 |
| 2003/0208201 A1 | | 11/2003 | Iida et al. | 606/51 |

FOREIGN PATENT DOCUMENTS

| | | |
|---|---|---|
| EP | 1 256 323 A2 | 11/2002 |
| JP | 5-5106 | 1/1993 |
| JP | 2000-254135 | 9/2000 |

(Continued)

OTHER PUBLICATIONS

International Search Report PCT/JP2005/010974 dated Jul. 4, 2005.

(Continued)

*Primary Examiner* — Anhtuan T Nguyen
*Assistant Examiner* — David Eastwood
(74) *Attorney, Agent, or Firm* — Ostrolenk Faber LLP

(57) ABSTRACT

An energy accessory includes an ultrasonic vibrator configured to generate ultrasonic vibration, an elongated probe whose proximal end is connected to the ultrasonic vibrator and configured to transmit the ultrasonic vibration generated by the ultrasonic vibrator from a proximal end side to a distal end side to apply the ultrasonic vibration to living tissue, a sheath provided on the proximal end side of the probe, a grasping portion provided on a distal end portion of the sheath and configured to be rotated with respect to the probe and brought into contact with the living tissue disposed on the side of the probe, whereby the living tissue is grasped in cooperation with the probe, and a treatment mode variable mechanism configured to change a treatment mode of a treatment with respect to the living tissue brought into contact with the grasping portion.

5 Claims, 21 Drawing Sheets

FOREIGN PATENT DOCUMENTS

| | | |
|---|---|---|
| JP | 2002-224133 | 2/2002 |
| JP | 2003-135479 | 5/2003 |
| JP | 2004-73891 | 3/2004 |
| JP | 2004073891 A * | 3/2004 |
| WO | WO 02/38057 A1 | 5/2002 |

OTHER PUBLICATIONS

International Preliminary Report on Patentability in corresponding PCT Appln. No. PCT/JP2005/010974 dated Dec. 20, 2006.

Search Report issued by European Patent Office in connection with corresponding application No. EP 05 75 0876 on Aug. 27, 2010.

Japanese Office Action mailed Jan. 18, 2011 in connection with corresponding Japanese Pantent Application No. 2006-514771.

Partial English translation of Japanese Office Action issued in connection with corresponding Japanese application provided as an explanation of prior art relevancy.

* cited by examiner

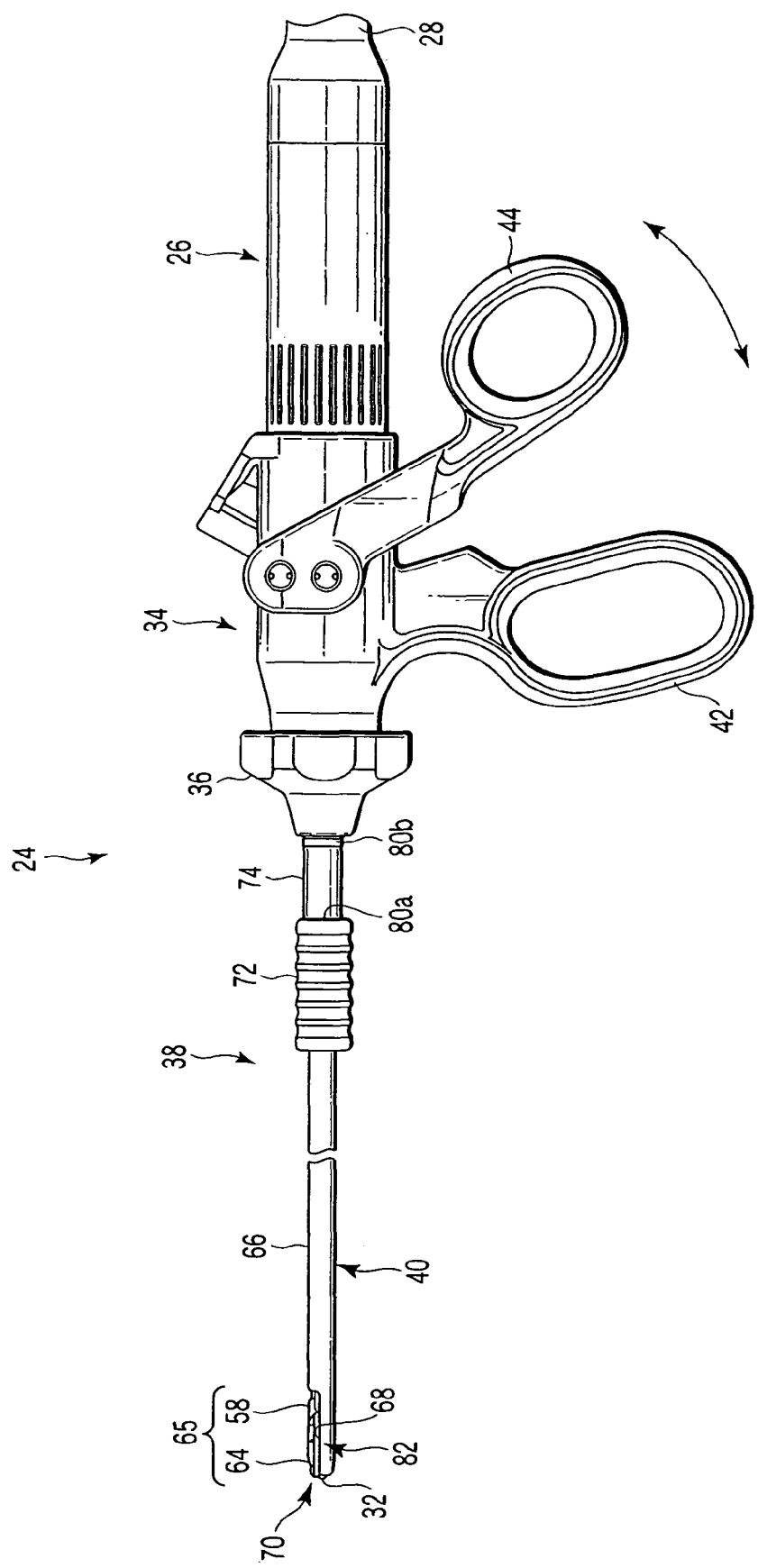
F I G. 5

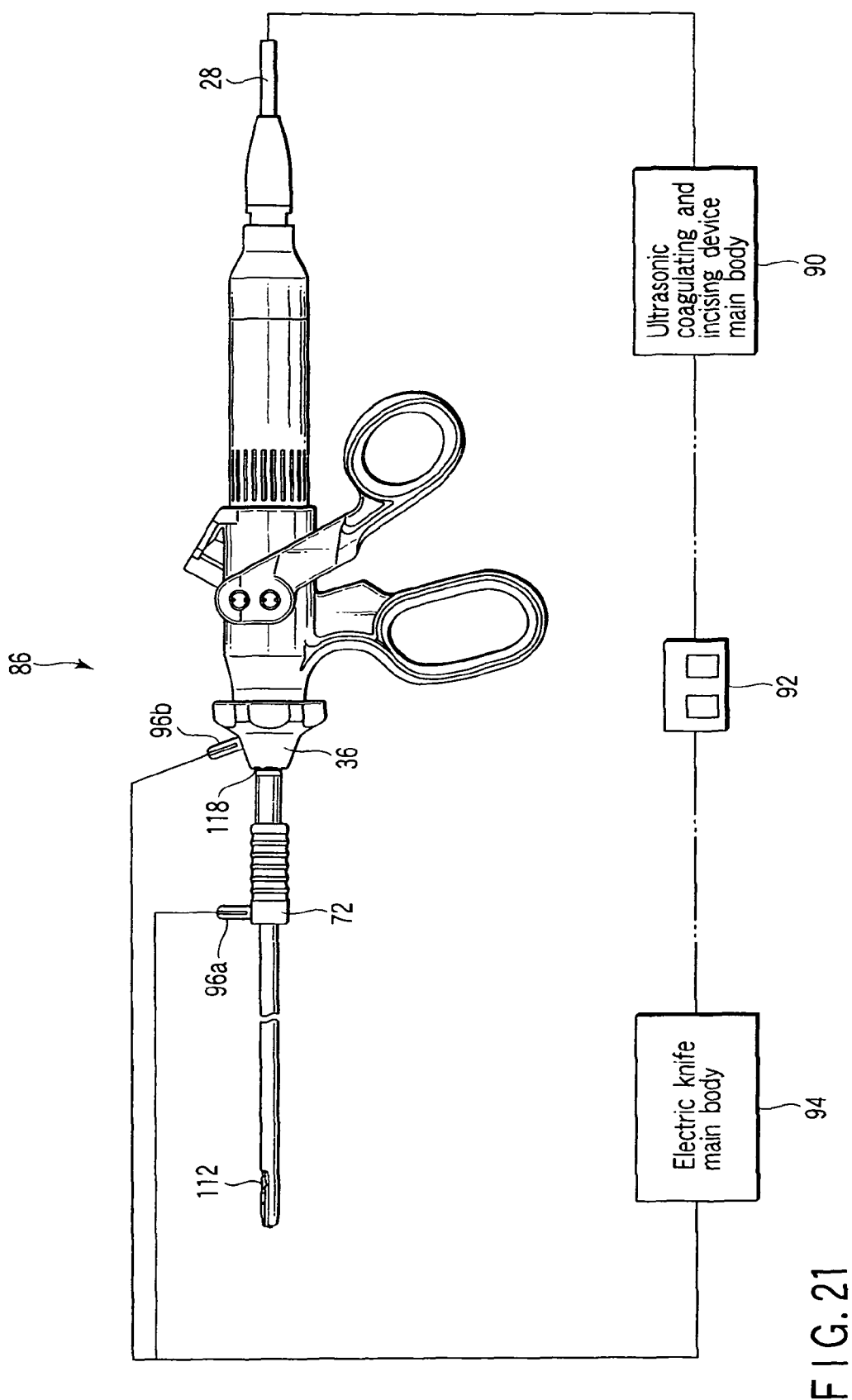
F I G. 21

US 7,909,824 B2

ENERGY ACCESSORY

CROSS REFERENCE TO RELATED APPLICATIONS

This is a Continuation Application of PCT Application No. PCT/JP2005/010974, filed Jun. 15, 2005, which was published under PCT Article 21(2) in Japanese.

This application is based upon and claims the benefit of priority from prior Japanese Patent Application No. 2004-176780, filed Jun. 15, 2004, the entire contents of which are incorporated herein by reference.

BACKGROUND OF THE INVENTION

1. Field of the Invention

The present invention relates to an energy accessory for use in coagulating or incising a living tissue in a surgical operation or the like.

2. Description of the Related Art

Heretofore, an energy accessory is used in applying energy to living tissue to coagulate or incise the tissue in an abdominal surgical operation, an endoscopic surgical operation or the like. As such an energy accessory, an ultrasonic accessory is used which applies ultrasonic vibration to the living tissue to coagulate or incise the tissue.

An example of such an ultrasonic accessory is disclosed in Jpn. Pat. Appln. KOKAI Publication No. 2002-224133. In this ultrasonic accessory, a probe is inserted into a sheath, and a distal end portion of the probe protrudes from a distal opening of the sheath. The probe amplifies and transmits the ultrasonic vibration generated by an ultrasonic vibrator. Moreover, the distal end portion of the sheath is provided with a grasping portion which is rotated with respect to the probe to grasp the living tissue in cooperation with the probe. When the grasping portion is rotated to abut on the probe, the grasping portion is brought into contact with the probe under a comparatively large constant contact pressure by a constant-force mechanism formed by a spring member or the like.

To treat the living tissue, the living tissue is grasped by the probe and the grasping portion, the ultrasonic vibration is applied from the probe to the grasped living tissue, and the living tissue is coagulated and incised. Here, a coagulating or incising capability with respect to the living tissue is changed depending on the grasping forces of the probe and the grasping portion with respect to the living tissue and the grasping forces are comparatively large and constant by a function of a constant force mechanism. Therefore, the living tissue is treated with the constant coagulating and incising capabilities while the incision has predominance over the coagulation.

Moreover, there is disclosed an ultrasonic accessory in U.S. Pat. No. 6,558,376. The ultrasonic accessory includes a probe, a sheath, and a grasping portion similar to those of the above ultrasonic accessory. Furthermore, in the distal end portion of the probe, support members are arranged on opposite sides of the probe and face the grasping portion, and these support members protrude toward the grasping portion with respect to the probe. When the living tissue is treated, the living tissue is supported by the support members on the opposite sides of the probe. Therefore, the coagulating capability is increased on opposite sides of an incised region of the living tissue.

BRIEF SUMMARY OF THE INVENTION

An embodiment of the present invention is directed to an energy accessory includes an ultrasonic vibrator configured to generate ultrasonic vibration, an elongated probe whose proximal end is connected to the ultrasonic vibrator and configured to transmit the ultrasonic vibration generated by the ultrasonic vibrator from a proximal end side to a distal end side to apply the ultrasonic vibration to living tissue, a sheath provided on the proximal end side of the probe, a grasping portion provided on a distal end portion of the sheath and configured to be rotated with respect to the probe and brought into contact with the living tissue disposed on the side of the probe, whereby the living tissue is grasped in cooperation with the probe, and a treatment mode variable mechanism configured to change a treatment mode of a treatment with respect to the living tissue brought into contact with the grasping portion.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 5 is a side view showing the energy accessory in its coagulation predominant state in the first embodiment of the present invention;

FIG. 21 is a schematic diagram showing an energy treatment system in a sixth embodiment of the present invention;

DETAILED DESCRIPTION OF THE INVENTION

A first embodiment of the present invention will be described hereinafter with reference to FIGS. 1 to 8C. In the present embodiment, an energy accessory is an ultrasonic accessory which applies ultrasonic vibration to living tissue to perform a coagulating or incising treatment on the living tissue. In the present embodiment, a treatment mode variable mechanism of the ultrasonic accessory switches a contact amount between a grasping member and a probe which grasp the living tissue to whereby switch the ultrasonic accessory between an incision predominant state to perform a coagulating and incising treatment which is an incision predominant treatment and an coagulation predominant state to perform a coagulating treatment which is a coagulation predominant treatment.

Figure 1:
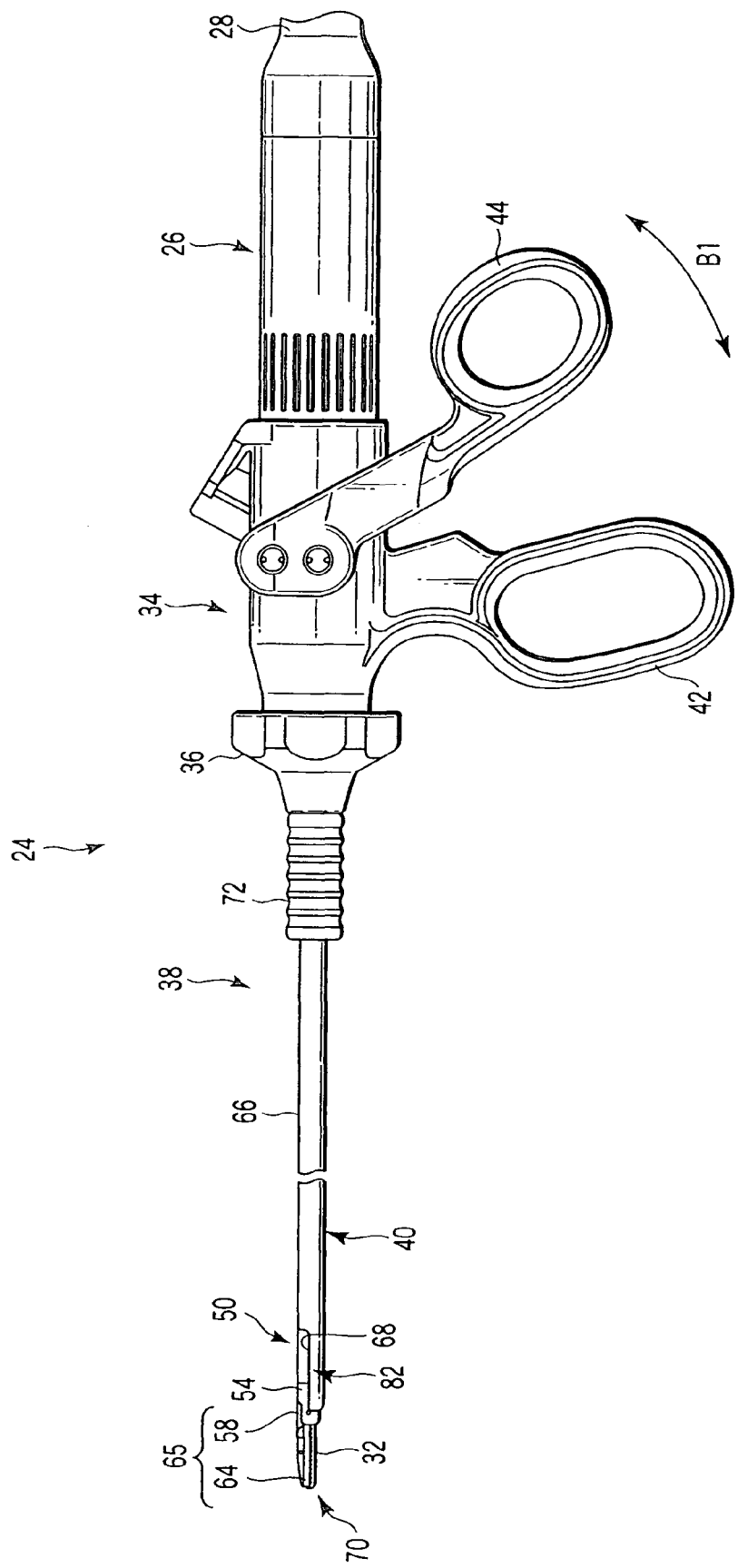
FIG. 1 is a side view showing an energy accessory in its incision predominant state in a first embodiment of the present invention.
Figure 2:
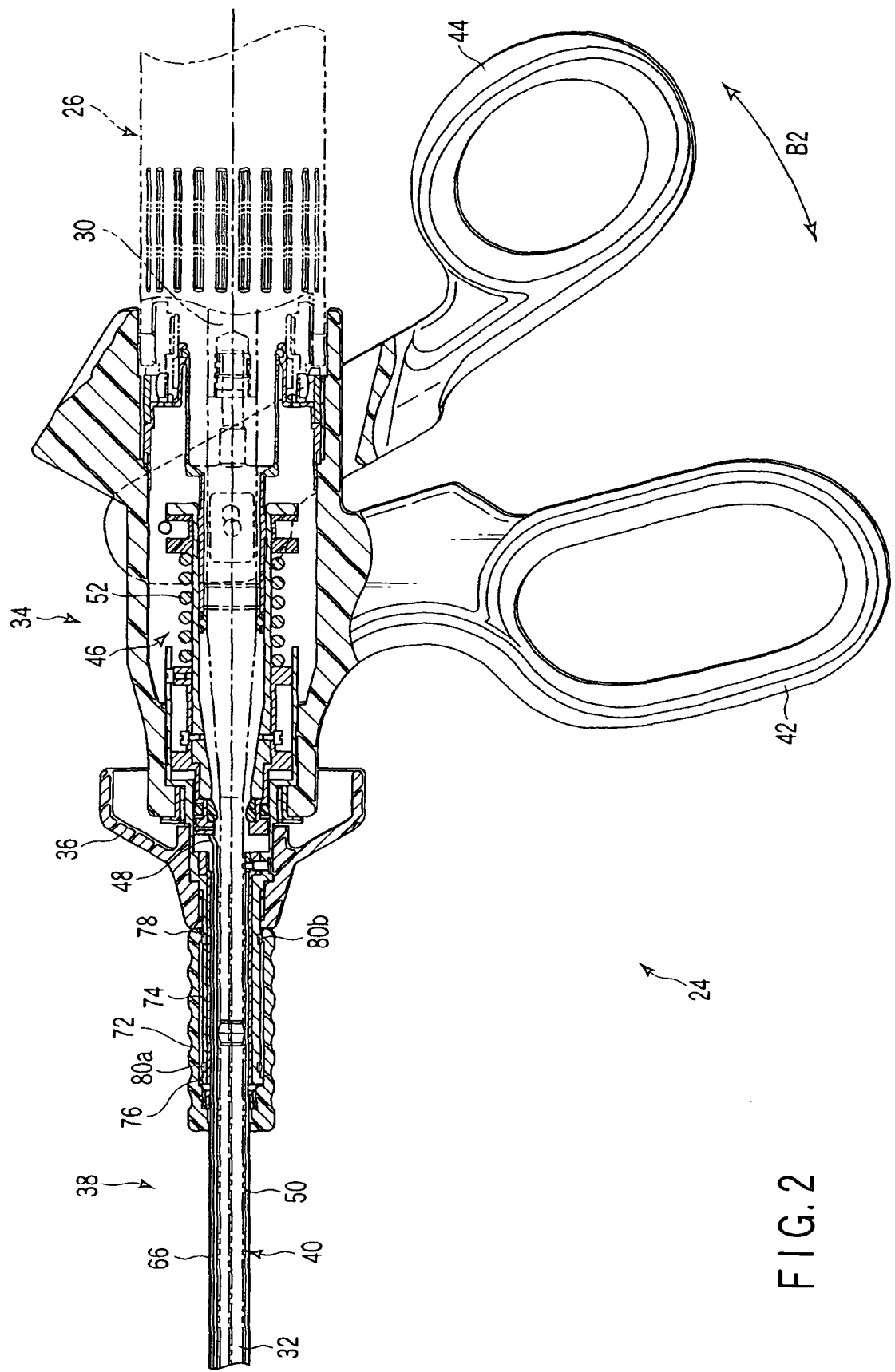
FIG. 2 is a longitudinal sectional view showing a handle unit of the energy accessory in its incision predominant state in the first embodiment of the present invention.

There will be described an ultrasonic accessory 24 in the incision predominant state with reference to FIGS. 1 to 4D. In the present embodiment, as shown in FIGS. 1 and 2, the ultrasonic accessory 24 has a vibrator unit 26 which contains an ultrasonic vibrator for converting electrical vibration into mechanical vibration. From a proximal end of this vibrator unit 26, a hand piece cord 28 is extended which supplies a vibration current to the ultrasonic vibrator. An extended end portion of this hand piece cord 28 is connected to a main body of an ultrasonic coagulating and incising device which generates a vibration current.

A distal end portion of the ultrasonic vibrator is provided with a horn 30 which amplifies the ultrasonic vibration generated by the ultrasonic vibrator. A distal end portion of this horn 30 is connected to a proximal end of an elongated probe 32 which transmits the ultrasonic vibration. The horn 30 and the probe 32 are integrally connected to each other by, for example, screwing a male screw portion formed on the proximal end of the probe 32 to a female screw portion formed in the distal end portion of the horn 30. A sectional shape of this probe 32 in a section which is perpendicular to a longitudinal direction is set in consideration of coagulating and incising capabilities with respect to the living tissue. In the present embodiment, the section is formed into a substantially flat shape in order to comparatively increase the coagulating capability.

Moreover, the proximal end of a handle unit 34 is assembled onto the distal end portion of the vibrator unit 26. The proximal end of a substantially cylindrical sheath unit 38 is assembled onto the distal end portion of this handle unit 34 via a rotary knob 36, and the sheath unit 38 can be rotated around a central axis of the unit. Moreover, the probe 32 connected to the ultrasonic vibrator of the vibrator unit 26 is inserted through the handle unit 34 and the sheath unit 38, and protruded from the distal end portion of the sheath unit 38. Thus, the sheath unit 38 and the probe 32 form an inserting portion 40 to be inserted into a patient's body cavity.

Here, a fixed handle 42 is integrally disposed on a main body portion of the handle unit 34, and a movable handle 44 is supported by a main body portion to be rotatable with respect to the fixed handle 42. That is, the movable handle 44 is openable and closeable with respect to the fixed handle 42 (see arrows B1 and B2 of FIGS. 1 and 2). The movable handle 44 is connected to a proximal end of a jaw driving shaft 48 via an operating force transmission mechanism 46, this jaw driving shaft 48 is inserted through a sheath 50 of the sheath unit 38 to be movable forwards and backwards, and the jaw driving shaft 48 protrudes from the distal end portion of the sheath 50. The movable handle 44 is opened and closed with respect to the fixed handle 42 to move forwards and backwards the jaw driving shaft 48 via the operating force transmission mechanism 46.

As shown in FIGS. 4A to 4D, a jaw holding portion 54 is disposed on the distal end portion of the sheath 50, and the proximal end of a jaw 58 is supported by the jaw holding portion 54 via a holding pin 56 which substantially crosses the central axis of the inserting portion 40 at right angles. Furthermore, the distal end portion of the jaw driving shaft 48 protruding from the distal end portion of the sheath 50 is disposed externally from the holding pin 56 on a pin distal end side, and connected pivotably on the proximal end of the jaw 58 via a rotation shaft 60 which is substantially parallel to the holding pin 56. The jaw driving shaft 48 moves forwards and backwards, whereby opening and closing the jaw 58 centering on the holding pin 56.

Moreover, a grasping member 64 is connected pivotably on an intermediate portion of the jaw 58 via a seesaw pin 62 which is substantially parallel to the holding pin 56 and the rotation shaft 60. This grasping member 64 is disposed facing the probe 32 which protrudes from the distal end portion of the sheath 50. Furthermore, when the jaw 58 is opened and closed by the jaw driving shaft 48, the grasping member 64 is opened and closed together with the jaw 58 with respect to the probe 32.

Referring to FIGS. 1 and 2, and FIGS. 4A to 4D, when the movable handle 44 is closed with respect to the fixed handle 42, the jaw driving shaft 48 is moved toward the distal end side, and the grasping member 64 is closed with respect to the probe 32. When the movable handle 44 is further closed after the grasping member 64 is brought into contact with the probe 32, an elastic member 52 of the operating force transmission mechanism 46 is contracted to generate a predetermined repulsive force, and the grasping member 64 is allowed to abut on the probe 32 under a predetermined contact pressure. This predetermined contact pressure is referred to as an incision predominant contact pressure. It is to be noted that the probe 32 is pressed and bent by the grasping member 64. However, since the grasping member 64 is rotated with respect to the jaw 58 to follow this bend, the whole grasping member 64 uniformly abuts on the probe 32.

Referring to FIGS. 4A to 4D, the grasping member 64 abuts on the probe 32 in this manner. To prevent the probe 32 from being worn by friction with the grasping member 64 during the ultrasonic vibration, the grasping member 64 is made of a low-friction-coefficient resin material such as PTFE. A pressing member 63 made of metal is disposed between the jaw 58 and the grasping member 64, and a desired connection strength is secured between the jaw 58 and the grasping member 64.

In this manner, the jaw 58 and the grasping member 64 form a grasping portion 65 which is rotated with respect to the probe 32, and this grasping portion 65 and the distal end portion of the probe 32 form a clamp portion 70 which grasps the living tissue. When the living tissue is grasped by the grasping member 64 and the probe 32, the living tissue is grasped with a comparatively large grasping force (perpendicular drag) corresponding to the incision predominant contact pressure between the grasping member 64 and the probe 32. Here, energy applied from the probe 32 to the grasped living tissue is proportional to the perpendicular drag, and an incising capability increases with the increase of the energy applied to the living tissue. The incision predominant contact pressure is set so that a coagulating and incising treatment which is an incision predominant treatment proceeds in the living tissue in a case where the ultrasonic vibration is applied from the probe 32 to the living tissue grasped with a grasping force corresponding to the incision predominant contact pressure.

A constitution will be described hereinafter in which the rotation of the grasping member 64 with respect to the probe 32 is limited, and the contact pressure between the grasping member 64 and the probe 32 is switched to switch the ultrasonic accessory 24 (see FIG. 1) between the incision predominant state and the coagulation predominant state.

An outer tube 66 is attached slidably along an outer periphery of the sheath 50 in a central-axis direction of the inserting portion 40. A distal end portion of the outer tube 66 is provided with an abutment portion 68 which abuts on the grasping member 64 to limit the rotation of the grasping member 64 with respect to the probe 32. When the ultrasonic accessory 24 (see FIG. 1) is brought into the incision predominant state, the outer tube 66 is positioned on a proximal end side with respect to the sheath 50, and the abutment portion 68 on the distal end portion of the outer tube 66 is positioned in a non-abutting position on the proximal end side of the clamp portion 70 wherein the abutment portion 68 is incapable of abutting on the grasping member 64.

Figure 3:
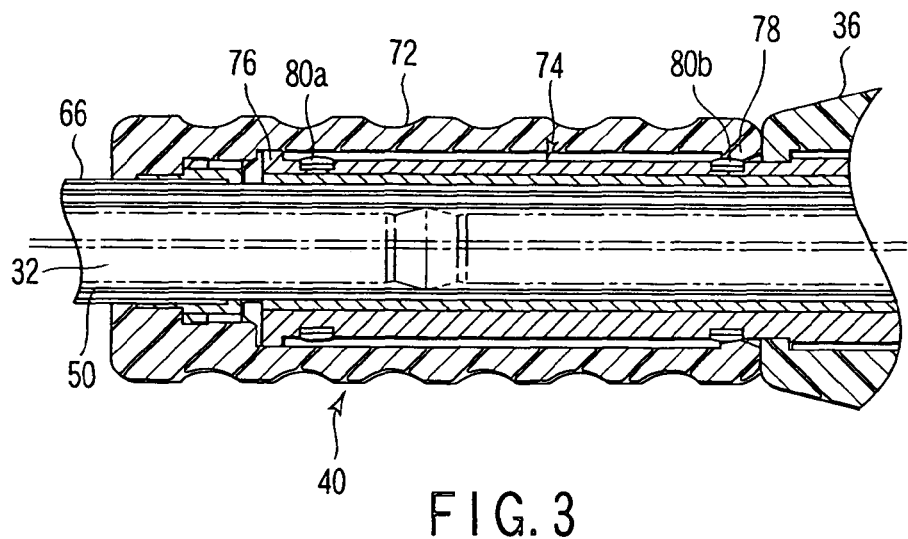
FIG. 3 is a longitudinal sectional view showing a proximal end of an inserting portion of the energy accessory in its incision predominant state in the first embodiment of the present invention.
Figure 4A:
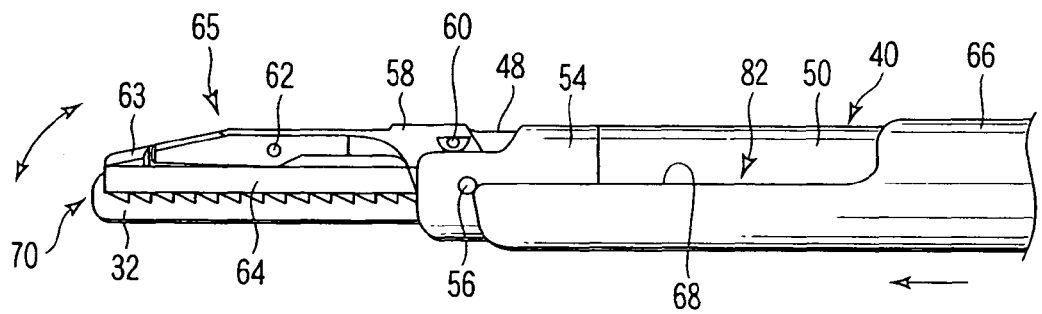
FIG. 4A is a side view showing a distal end portion of the inserting portion of the energy accessory in its incision predominant state in the first embodiment of the present invention.
Figure 4B:
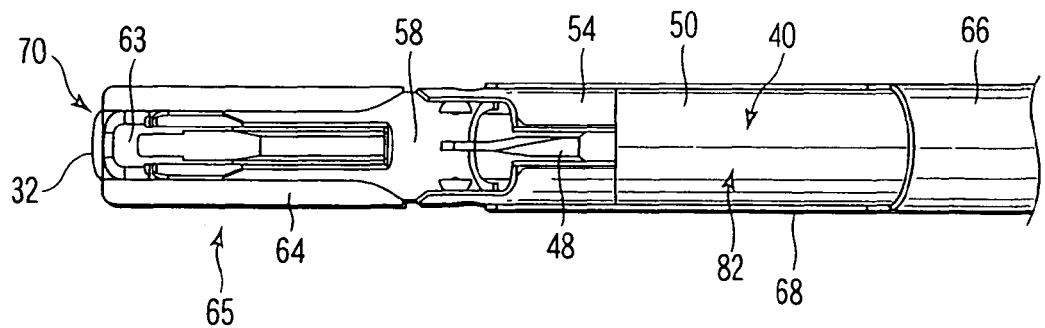
FIG. 4B is a top plan view showing the distal end portion of the inserting portion of the energy accessory in its incision predominant state in the first embodiment of the present invention.
Figure 4C:
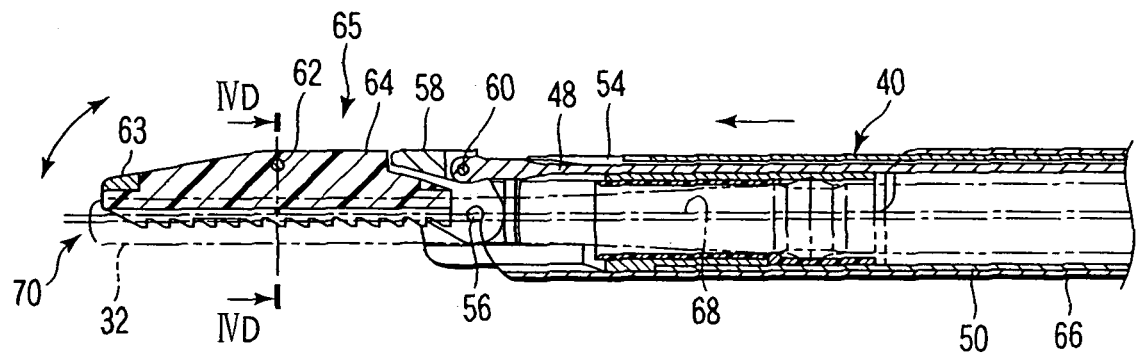
FIG. 4C is a longitudinal sectional view showing the distal end portion of the inserting portion of the energy accessory in its incision predominant state in the first embodiment of the present invention.
Figure 4D:
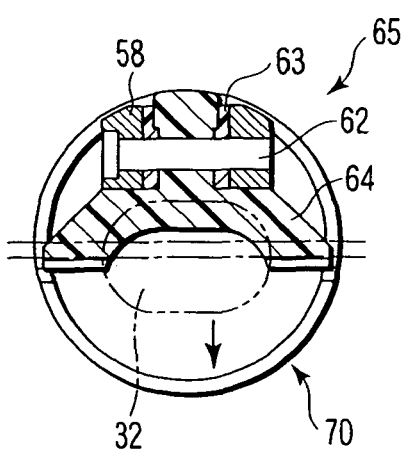
FIG. 4D is a lateral sectional view cut along the IVD-IVD line of FIG. 4C and showing the distal end portion of the inserting portion of the energy accessory in its incision predominant state in the first embodiment of the present invention.
Figure 6:
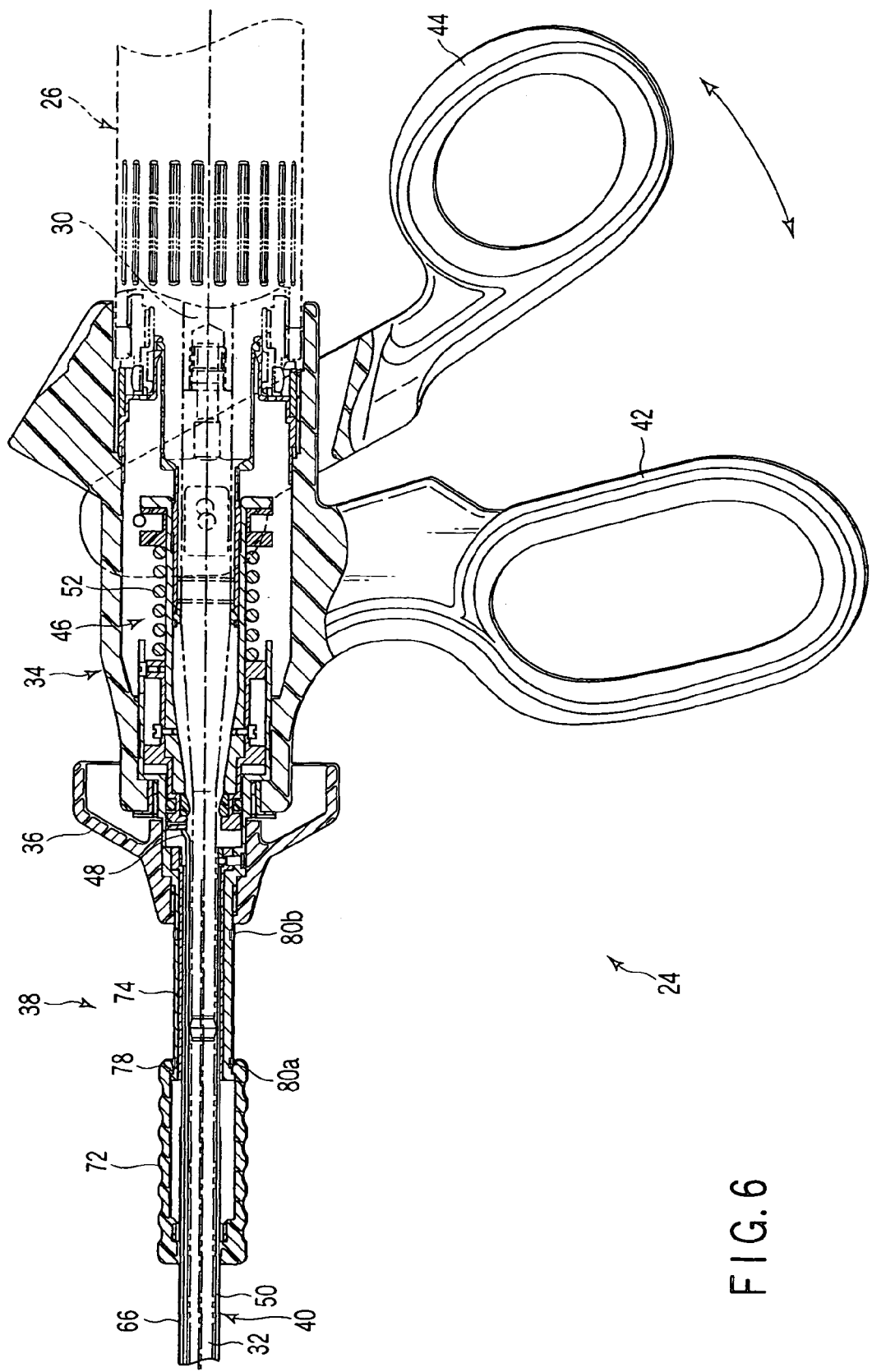
FIG. 6 is a longitudinal sectional view showing the handle unit of the energy accessory in its coagulation predominant state in the first embodiment of the present invention.

As shown in FIG. 3, a proximal end of the outer tube 66 is fitted into and fixed to the distal end portion of a substantially cylindrical operation knob 72 disposed on the proximal end of the sheath 50. This operation knob 72 is fitted on an outer periphery of a rotary connecting member 74 which is protruded from the distal end portion of the rotary knob 36, and fitted on an outer periphery of the proximal end of the sheath 50. Moreover, the operation knob 72 is slidable in the central-axis direction of the inserting portion 40 with respect to the rotary connecting member 74, and the operation knob 72 can be positioned in either a proximal end side fixing position on the proximal end side or a distal end side fixing position on the distal end side with respect to the rotary connecting member 74. When the ultrasonic accessory 24 (see FIG. 1) is brought into the incision predominant state, the operation knob 72 is positioned in the proximal end side fixing position on the proximal end side with respect to the rotary connecting member 74.

A constitution will be described in which the operation knob 72 is positioned in either the proximal end side fixing position or the distal end side fixing position with respect to the rotary connecting member 74. A support protruding portion 76 protruding outwards is extended over the whole outer peripheral surface of the distal end portion of the rotary connecting member 74. An engagement protruding portion 78 protruding inwards is extended over the whole inner peripheral surface of the proximal end of the operation knob 72. The support protruding portion 76 of the rotary connecting member 74 abuts on the inner peripheral surface of the operation knob 72 and the engagement protruding portion 78 of the operation knob 72 abuts on the outer peripheral surface of the rotary connecting member 74, whereby the operation knob 72 is supported by the rotary connecting member 74. A first C-ring 80a is disposed on the distal end side, and a second C-ring 80b is disposed on the proximal end side at a predetermined distance from the first C-ring in the central-axis direction of the sheath 50 on the outer peripheral surface of the rotary connecting member 74 on the proximal end side of the support protruding portion 76. When the operation knob 72 is slid with respect to the rotary connecting member 74, and either of the first C-ring 80a and the second C-ring 80b of the rotary connecting member 74 is engaged with the engagement protruding portion 78 of the operation knob 72, the operation knob 72 is positioned either of the distal end side fixing position and the proximal end side fixing position with respect to the rotary connecting member 74.

It is to be noted that a constitution for positioning the operation knob 72 with respect to the rotary connecting member 74 is not limited to a C-ring system by the above-described C-ring, and a system by a snap fit, a key groove or the like may be used.

Figure 7:
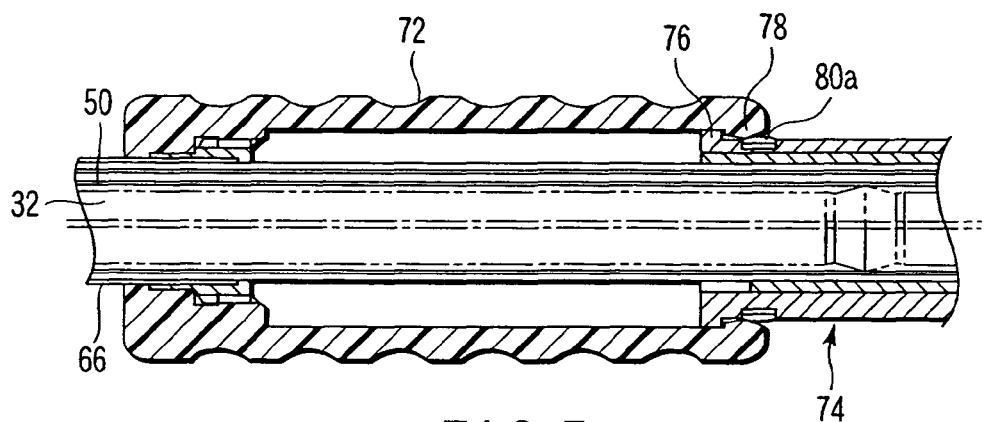
FIG. 7 is a longitudinal sectional view showing the proximal end of the inserting portion of the energy accessory in its coagulation predominant state in the first embodiment of the present invention.
Figure 8A:
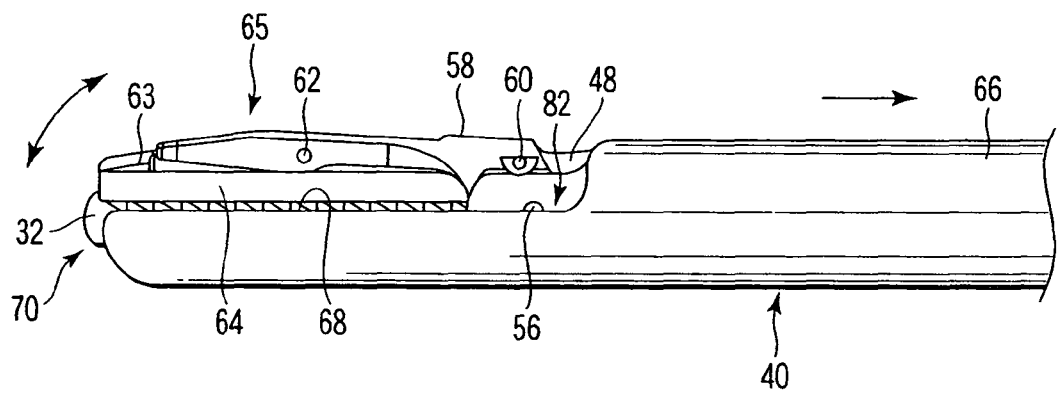
FIG. 8A is a side view showing the distal end portion of the inserting portion of the energy accessory in its coagulation predominant state in the first embodiment of the present invention.
Figure 8B:
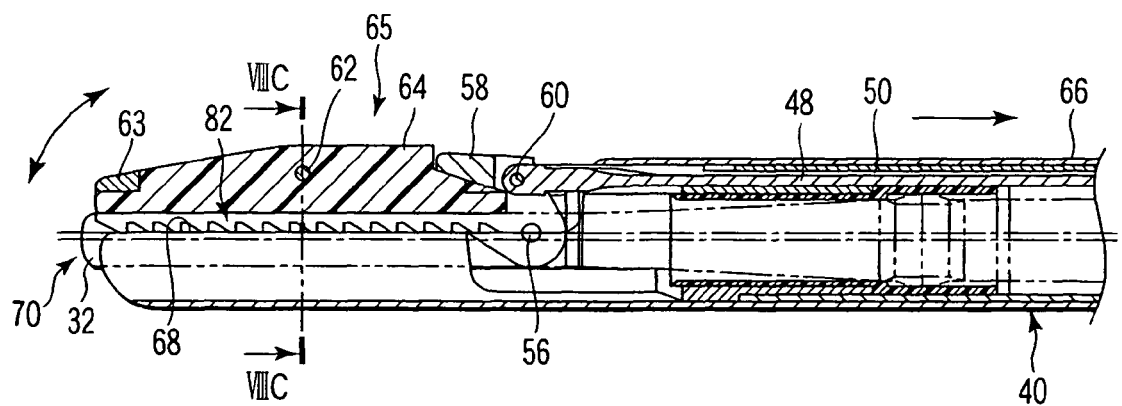
FIG. 8B is a longitudinal sectional view showing the distal end portion of the inserting portion of the energy accessory in the coagulation predominant state in the first embodiment of the present invention.
Figure 8C:
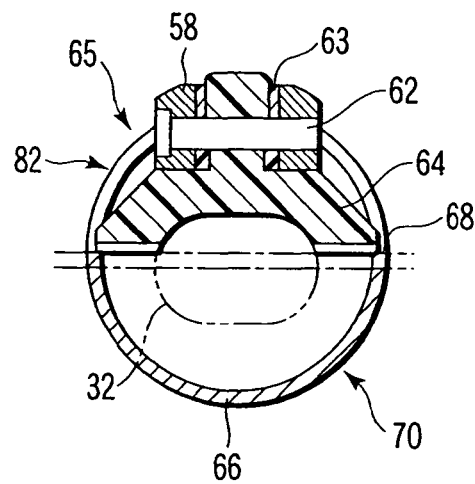
FIG. 8C is a lateral sectional view cut along the VIIIC-VIIIC line of FIG. 8B and showing the distal end portion of the inserting portion of the energy accessory in its coagulation predominant state in the first embodiment of the present invention.

Subsequently, there will be described the ultrasonic accessory 24 in a coagulating predominant state with reference to FIGS. 5 to 8C. In the coagulating predominant state, as shown in FIG. 7, the operation knob 72 is positioned in the distal end side fixing position with respect to the rotary connecting member 74. Moreover, as shown in FIGS. 8A to 8C, the outer tube 66 is positioned on the distal end side with respect to the sheath 50, and the distal end portion of the outer tube 66 is positioned in the clamp portion 70. The distal end portion of the sheath 50 is provided with a notch portion 82 on the side of the grasping member 64, and this notch portion 82 forms the abutment portion 68 which is an elongated double-face portion extending in the central-axis direction of the inserting portion 40 on opposite sides of the probe 32 and facing opposite end portions of the grasping member 64. This abutment portion 68 is positioned in an abutting position wherein the abutment portion 68 abuts on the grasping member 64 in a case where the ultrasonic accessory 24 (see FIG. 5) is brought into the coagulating predominant state.

In a case where the grasping member 64 is closed with respect to the probe 32, the grasping member 64 abut on the abutment portion 68 so that a rotation of the grasping member 64 is limited immediately before the grasping member 64 comes into contact with the probe 32. It is to be noted that since the grasping member 64 is rotated with respect to the jaw 58, the whole opposite end portions of the grasping member 64 uniformly abut on the abutment portion 68. In this state, a predetermined clearance is formed between the probe 32 and the grasping member 64, the probe 32 is not brought into contact with the grasping member 64, and the contact pressure between the probe 32 and the grasping member 64 is substantially zero. This contact pressure is referred to as the coagulating predominant contact pressure.

In a case where the ultrasonic accessory 24 (see FIG. 5) is brought into the coagulating predominant state, the grasping member 64, the probe 32, and the abutment portion 68 grasp the living tissue. Here, the living tissue is grasped mainly by the opposite-side end portions of the grasping member 64 and the abutment portion 68. Moreover, the living tissue is grasped by the grasping member 64 and the probe 32 with a comparatively small grasping portion corresponding to the coagulating predominant contact pressure between the grasping member 64 and the probe 32. The coagulating predominant contact pressure is substantially zero, and the energy applied to the living tissue grasped with the corresponding grasping force is insufficient for proceeding with the incising treatment, but the energy is sufficient for proceeding with the coagulating treatment. Therefore, when the ultrasonic vibration is applied from the probe 32 to the living tissue grasped with the grasping force corresponding to the coagulating predominant contact pressure, the incising treatment does not proceed, and only the coagulating treatment proceeds in the living tissue. In the present embodiment, the contact pressure between the grasping member 64 and the probe 32 is adjusted to adjust incising and coagulating capabilities at a time when the ultrasonic vibration is applied to the living tissue grasped by the grasping member 64 and the probe 32. In addition, it is possible to adjust the incising and coagulating capabilities with respect to the living tissue by adjusting a contact area between the grasping member 64 and the probe 32, the shortest distance therebetween or the like. An amount, such as the contact pressure, the contact area, or the shortest distance, is generically referred to as a contact amount. The contact amount is adjusted by adjusting a rotatable amount of the grasping portion 65 and indicates a contact state between the grasping portion 65 and the probe 32, and the incising and coagulating capabilities with respect to the living tissue is adjusted through the adjustment for the contact amount.

In this manner, in the present embodiment, the outer tube 66 forms an outer member attached slidably along an outer periphery of the sheath 50 in a longitudinal-axis direction of the probe 32. The operation knob 72 and the outer tube 66 forms a movement mechanism which moves the abutment portion 68, changes an abutting state between the grasping portion 65 and the abutment portion 68, adjusts the rotatable amount of the grasping portion 65, and adjusts the contact amount between the grasping portion 65 and the probe 32. Although the cylindrical outer tube 66 is used as the outer member in the present embodiment, a shape of the outer member may be any shape as long as the member can be attached slidably along the outer periphery of the sheath 50 in the longitudinal-axis direction of the probe 32.

Next, there will be described an operation of the ultrasonic accessory 24 in the present embodiment. When the living tissue is subjected to the coagulating and incising treatment, the ultrasonic accessory 24 is switched to the incision predominant state. That is, the operation knob 72 is positioned in the proximal end side fixing position with respect to the rotary connecting member 74 to position the outer tube 66 on the proximal end side, and the abutment portion 68 is retreated to a non-abutting position on the proximal end side of the clamp portion 70.

Moreover, the movable handle 44 is opened and closed with respect to the fixed handle 42 to move the jaw driving shaft 48 forwards and backwards via the operating force transmission mechanism 46, and the grasping member 64 is opened and closed with respect to the probe 32 to grasp the living tissue by the probe 32 and the grasping member 64. Here, when the ultrasonic accessory 24 is brought into the incision predominant state, and the probe 32 is brought into contact with the grasping member 64, the incision predominant contact pressure is generated between the probe 32 and the grasping member 64. Therefore, the living tissue is grasped by the grasping member 64 and the probe 32 with a comparatively large grasping force corresponding to the incision predominant contact pressure between the grasping member 64 and the probe 32. In this state, the ultrasonic vibration is generated by the ultrasonic vibrator, the ultrasonic vibration is transmitted by the probe 32, the ultrasonic vibration is applied from the distal end portion of the probe 32 to the living tissue, and the living tissue is subject the coagulating and incising treatment.

When the living tissue is subjected to the coagulating treatment, the ultrasonic accessory 24 is switched to the coagulating predominant state. That is, the operation knob 72 is positioned in the distal end side fixing position with respect to the rotary connecting member 74 to position the outer tube 66 on the distal end side, and the abutment portion 68 is positioned in the abutting position of the clamp portion 70.

Furthermore, the movable handle 44 is opened and closed with respect to the fixed handle 42, the grasping member 64 is opened and closed with respect to the probe 32 and the abutment portion 68, and the living tissue is grasped by the probe 32, the abutment portion 68, and the grasping member 64. In this case, the living tissue is grasped mainly by the abutment portion 68 and the grasping member 64. Here, in a case where the ultrasonic accessory 24 is brought into the coagulating predominant state, the rotation of the grasping member 64 is limited by the abutment portion 68, and the probe 32 and the grasping member 64 are brought into a non-contact state, the coagulating predominant contact pressure is generated between the probe 32 and the grasping member 64. Therefore, the living tissue is grasped by the grasping member 64 and the probe 32 with a comparatively small grasping force corresponding to the coagulating predominant contact pressure between the grasping member 64 and the probe 32. When the ultrasonic vibration is applied from the distal end portion of the probe 32 to the living tissue in this state, the incising treatment does not proceed in the living tissue, and a powerful coagulating treatment is performed on the living tissue.

It is to be noted that the living tissue is grasped mainly by the abutment portion 68 and the grasping member 64. Therefore, even in a case where the distal end portion of the inserting portion 40 is lifted up from the probe 32 side toward the grasping portion 65 side during the coagulating treatment, a force to tear the living tissue is not applied from the abutment portion 68 to the living tissue, and the probe 32 is not strongly pressed by the living tissue. Therefore, the coagulating treatment does not shift to the coagulating and incising treatment.

Therefore, in the present embodiment, the ultrasonic accessory 24 produces the following effect. In the present embodiment, when the living tissue is grasped by the grasping portion 65 and the probe 32 to treat the living tissue, the abutment portion 68 is moved so that the abutting state between the grasping portion 65 and the abutment portion 68 is changed to adjust the rotatable amount of the grasping portion 65. So the contact amount between the grasping portion 65 and the probe 32 is adjusted, whereby the incising and coagulating capabilities with respect to the living tissue are adjusted. Thus, the coagulating capability and the incising capability can be adjusted in the integral ultrasonic accessory 24, and operation efficiency is increased.

Figure 9A:
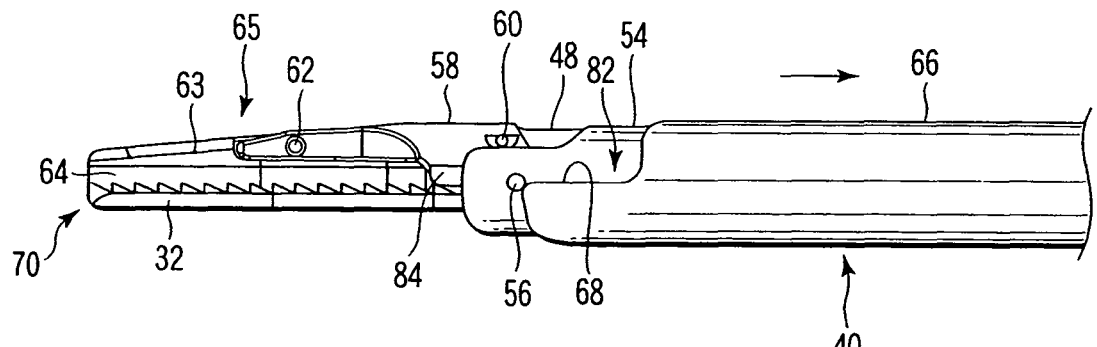
FIG. 9A is a side view showing a distal end portion of an inserting portion of an energy accessory in its incision predominant state in a second embodiment of the present invention.
Figure 9B:
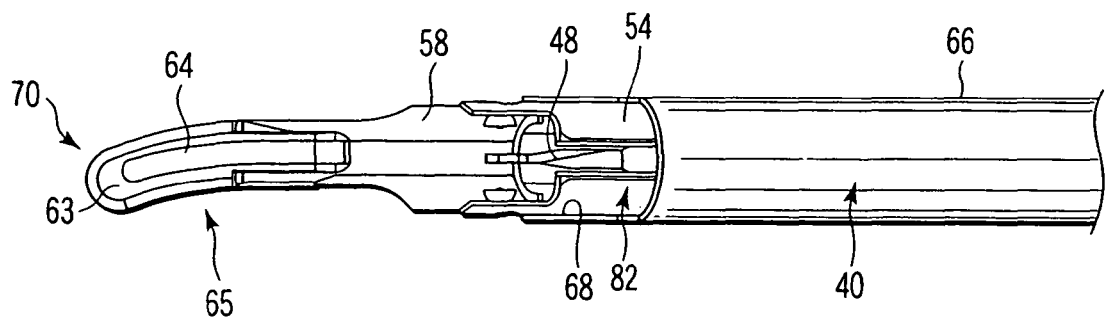
FIG. 9B is a top plan view showing the distal end portion of the inserting portion of the energy accessory in its incision predominant state in the second embodiment of the present invention.
Figure 9C:
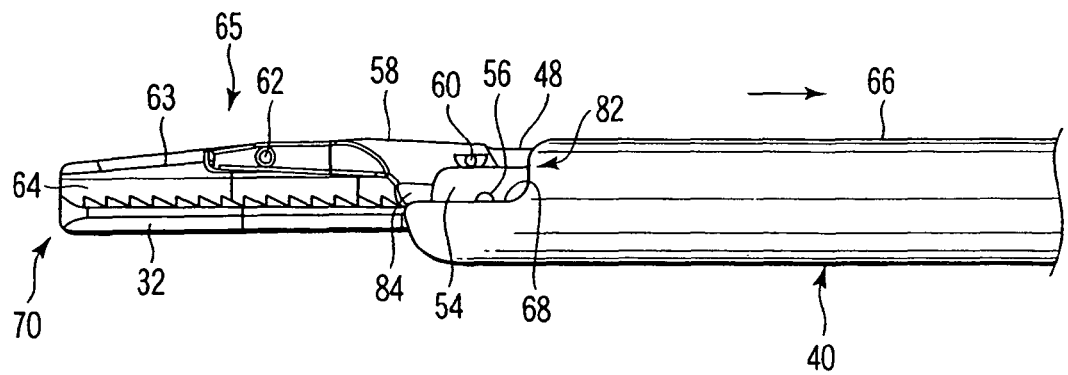
FIG. 9C is a side view showing the distal end portion of the inserting portion of the energy accessory in its coagulation predominant state in the second embodiment of the present invention.

FIGS. 9A to 9C show a second embodiment of the present invention. A constitution having a function similar to that of the first embodiment is denoted with the same reference numerous, and description thereof is omitted. In the present embodiment, an abutment portion 68 of an outer tube 66 is allowed to abut on an engagement portion 84 which protrudes from a proximal end of a grasping member 64 toward a probe 32, instead of the whole grasping member 64. It is to be noted that in the present embodiment, a grasping portion 65 and the probe 32 have shapes moderately curved toward the distal end side.

Next, there will be described an operation of an ultrasonic accessory 24 of the present embodiment. In a case where a coagulating and incising treatment is performed with the ultrasonic accessory 24, the ultrasonic accessory 24 is switched to an incision predominant state. That is, a distal end portion of the outer tube 66 is positioned on a proximal end side of a clamp portion 70, the abutment portion 68 is positioned in a non-abutting position wherein the abutment portion 68 is incapable of abutting on the engagement portion 84, and a contact pressure between the probe 32 and the grasping member 64 is adjusted into an incision predominant contact pressure. On the other hand, in a case where the coagulating treatment is performed with the ultrasonic accessory 24, the ultrasonic accessory 24 is switched to a coagulating predominant state. That is, the distal end portion of the outer tube 66 is positioned in the clamp portion 70 so that the abutment portion 68 is positioned in an abutting position wherein the abutment portion 68 is capable of abutting on the engagement portion 84. The abutment portion 68 abuts on the engagement portion 84 to adjust a rotation amount of the grasping member 64, and the contact pressure between the probe 32 and the grasping member 64 is adjusted into a coagulating predominant contact pressure.

Therefore, in the present embodiment, the ultrasonic accessory 24 produces the following effect. In the present embodiment, since the only engagement portion 84 on the proximal end of the grasping member 64 is allowed to abut on the abutment portion 68, unlike the first embodiment, the distal end side of the grasping member 64 does not have to be provided with a member allowed to abut on the abutment portion 68. Therefore, a width of the grasping member 64 can be reduced, and the clamp portion 70 can be miniaturized. Unlike the first embodiment, the clamp portion 70 on the distal end side is not configured to be covered with the outer tube 66 in the coagulating predominant state, restrictions on a shape of the clamp portion 70 are reduced, and degree of freedom in design is increased.

Figure 10A:
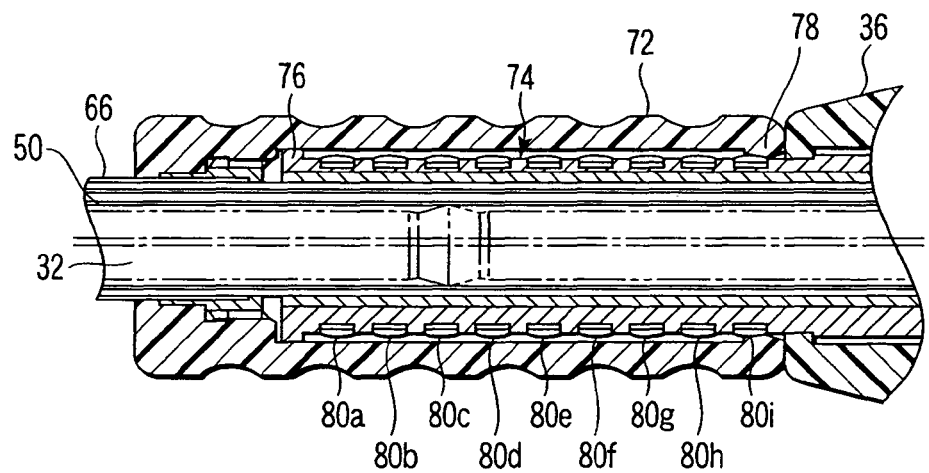
FIG. 10A is a longitudinal sectional view showing a proximal end of an inserting portion of an energy accessory in a third embodiment of the present invention.
Figure 10B:
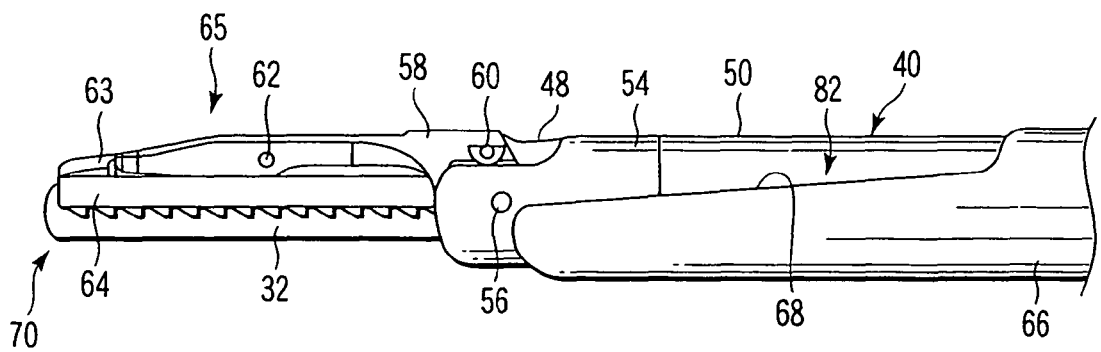
FIG. 10B is a side view showing a distal end portion of the inserting portion of the energy accessory in the third embodiment of the present invention.

FIGS. 10A and 10B show a third embodiment of the present invention. A constitution having a function similar to that of the first embodiment is denoted with the same reference numerous, and description is omitted. In the present embodiment, on an outer peripheral surface of a rotary connecting member 74, three or more C-rings 80a, 80b, ..., 80h, and 80i for engagement with an engagement protruding portion 78 of an operation knob 72 are arranged side by side at distances in a central-axis direction of an inserting portion 40. In the present embodiment, the first to ninth C-rings 80a, 80b, ..., 80h, and 80i are arranged side by side from a distal end side toward a proximal end side. That is, the operation knob 72 can be positioned in any of first to ninth fixing positions arranged from the distal end side toward the proximal end side.

In a distal end portion of an outer tube 66, a notch portion 82 forms an abutment portion 68 which is a slope inclined from a probe 32 side toward a grasping portion 65 side and from the distal end side toward the proximal end side. Since the operation knob 72 is positioned in one of the first to ninth fixing positions, a grasping member 64 abuts on corresponding one of the predetermined nine places arranged from the distal end side toward the proximal end side in the abutment portion 68. These predetermined nine places are referred to as first to ninth abutting positions of the abutment portion 68. The first to ninth abutting positions are displaced from the probe 32 side toward the grasping portion 65 side in multi stages. Therefore, in a case where the grasping member 64 abuts on the first to ninth abutting positions, a rotatable amount is reduced in multi stages, a contact pressure between the grasping member 64 and the probe 32 is also reduced in multi stages, and an incising capability is reduced in multi stages.

In the ultrasonic accessory 24 of the present embodiment, when the operation knob 72 is positioned in any of the first to ninth fixing positions, the incising and coagulating capabilities of the ultrasonic accessory 24 can be set in multi stages. Therefore, it is possible to treat living tissue in various treatment modes.

Figure 11:
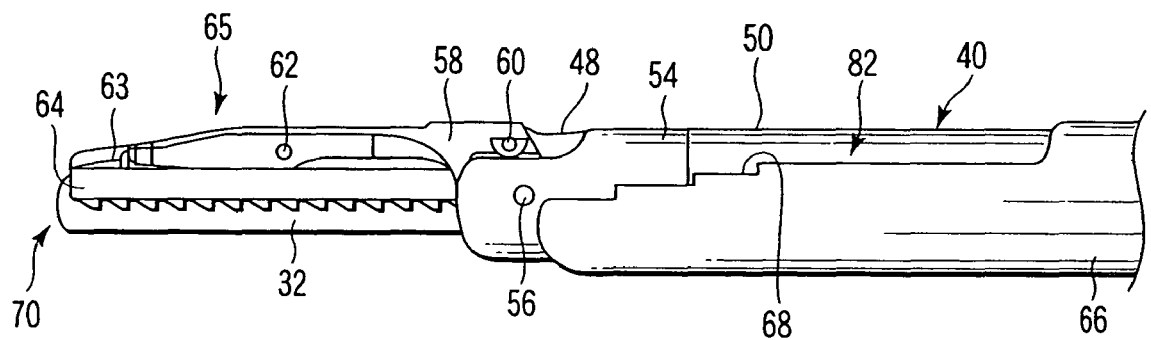
FIG. 11 is a side view showing an energy accessory in a fourth embodiment of the present invention.

FIG. 11 shows a fourth embodiment of the present invention. A constitution having a function similar to that of the first embodiment is denoted with the same reference numerous, and description thereof is omitted. In the present embodiment, in a distal end portion of an outer tube 66, a notch portion 82 forms an abutment portion 68 having a staircase shape ascending from a probe 32 side toward a grasping portion 65 side and from the distal end side toward the proximal end side. That is, the abutment portion 68 is provided with a plurality of stepped abutting positions displaced in multi stages from the probe 32 side toward the grasping portion 65 side and from the distal end side toward the proximal end side. As is the same in the third embodiment, incising capabilities in a case where a grasping member 64 abuts on these abutting positions are reduced in multi stages toward the proximal end side.

As described above, in an ultrasonic accessory 24 of the present embodiment, since an operation knob 72 is moved in a central-axis direction of an inserting portion 40, and the grasping member 64 is allowed to abut on any of a plurality of abutting positions of the abutment portion 68, it is possible to set the incising capability and a coagulating capability of the ultrasonic accessory 24 in multi stages. In consequence, it is possible to treat living tissue in various treatment modes.

It is to be noted that in the present embodiment, in the same manner as in the third embodiment, a rotary connecting member 74 may be provided with three or more C-rings so that in a case where the operation knob 72 is positioned in a predetermined fixing position the grasping member 64 abuts on the corresponding abutting position.

In the above respective embodiments, since the operation knob 72 is engaged with the rotary connecting member 74 by a D-cut, a key groove or the like, the outer tube 66 and the operation knob 72 are positioned around a central axis with respect to the sheath 50 and the rotary connecting member 74.

FIGS. 12 to 20C show a fifth embodiment of the present invention. A constitution having a function similar to that of the first embodiment is denoted with the same reference numerous, and description thereof is omitted. In the present embodiment, a treatment mode variable mechanism switches an energy accessory between an incision predominant state to perform coagulating and incising treatment which is an incision predominant treatment by use of ultrasonic vibration and a coagulating predominant state to perform a coagulating treatment which is a coagulation predominant treatment by use of a bipolar high frequency current.

Figure 12:
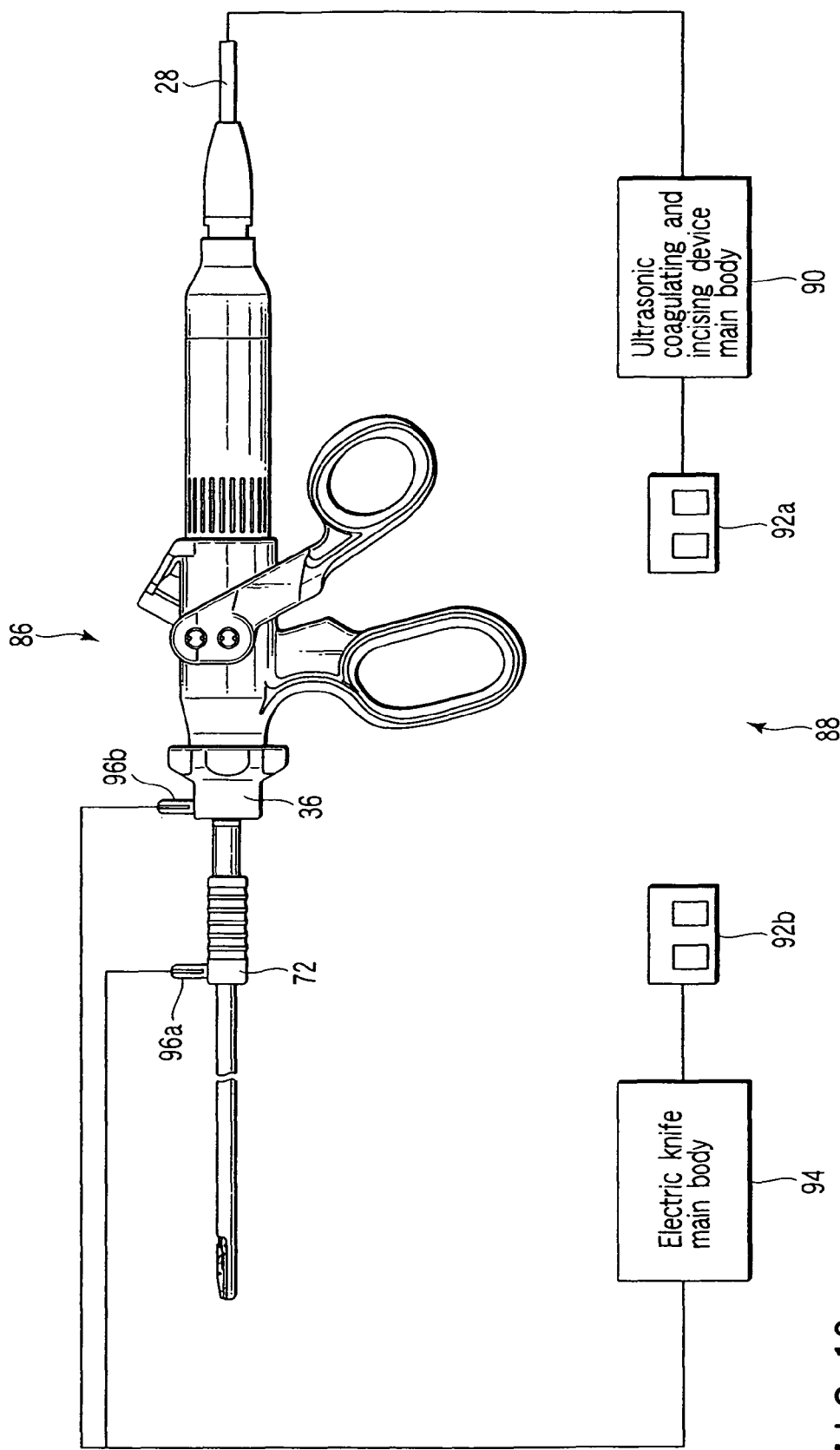
FIG. 12 is a schematic diagram showing an energy treatment system in a fifth embodiment of the present invention.

In the present embodiment, as shown in FIG. 12, an energy treatment system 88 has an ultrasonic coagulating and incising device main body 90 which is connected to an extended end portion of a hand piece cord 28 of an energy accessory 86 to supply a vibration current to an ultrasonic vibrator. This ultrasonic coagulating and incising device main body 90 is connected to an ultrasonic foot switch 92*a* for operating the ultrasonic coagulating and incising device main body 90.

Moreover, the energy treatment system 88 of the present embodiment has an electric knife main body 94 for supplying a high frequency current to the energy accessory 86. This electric knife main body 94 is connected to first and second connection terminals 96*a*, 96*b* disposed in the energy accessory 86, whereby forming a circuit for supplying the high frequency current to living tissue. The electric knife main body 94 is connected to a high frequency foot switch 92*b* for operating the electric knife main body 94.

Figure 13:
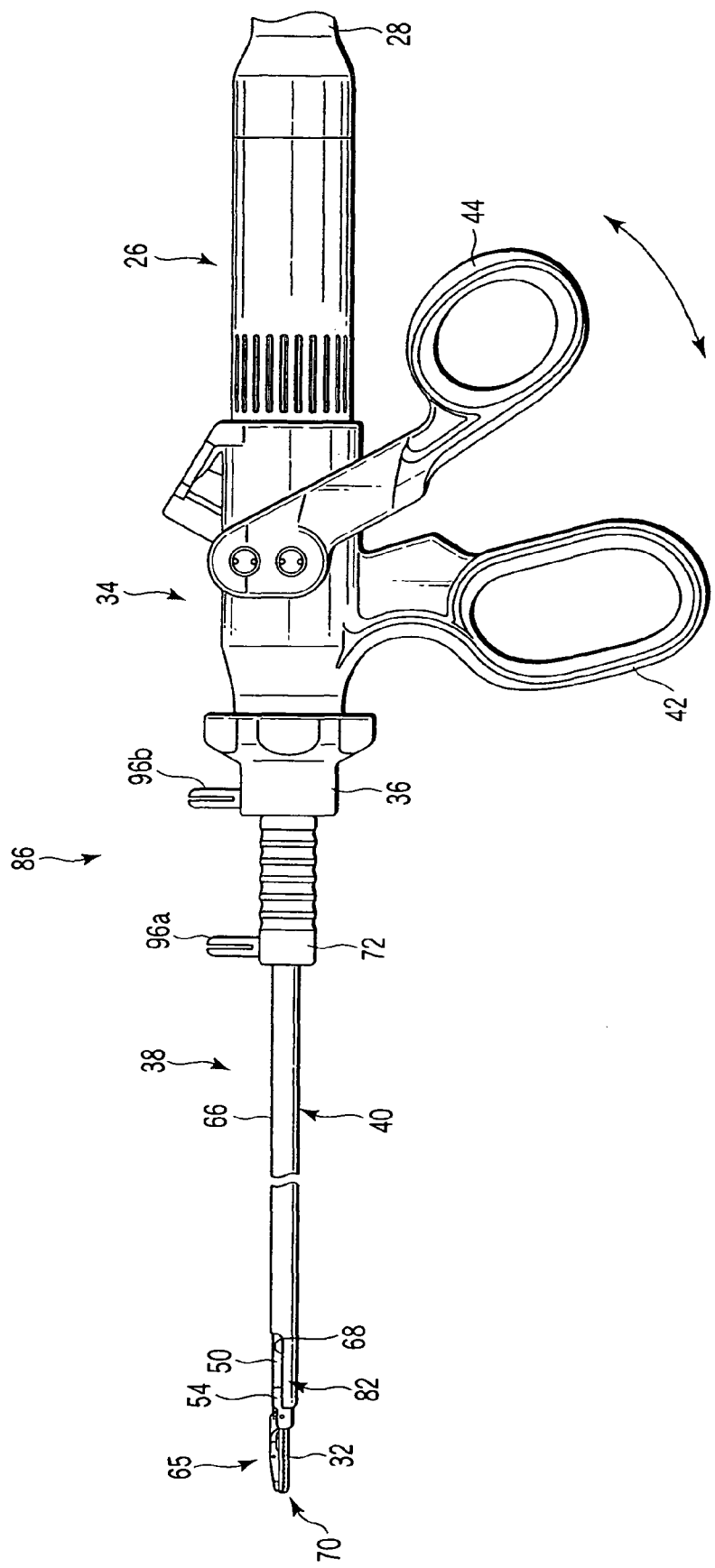
FIG. 13 is a side view showing an energy accessory in its incision predominant state in the fifth embodiment of the present invention.
Figure 14:
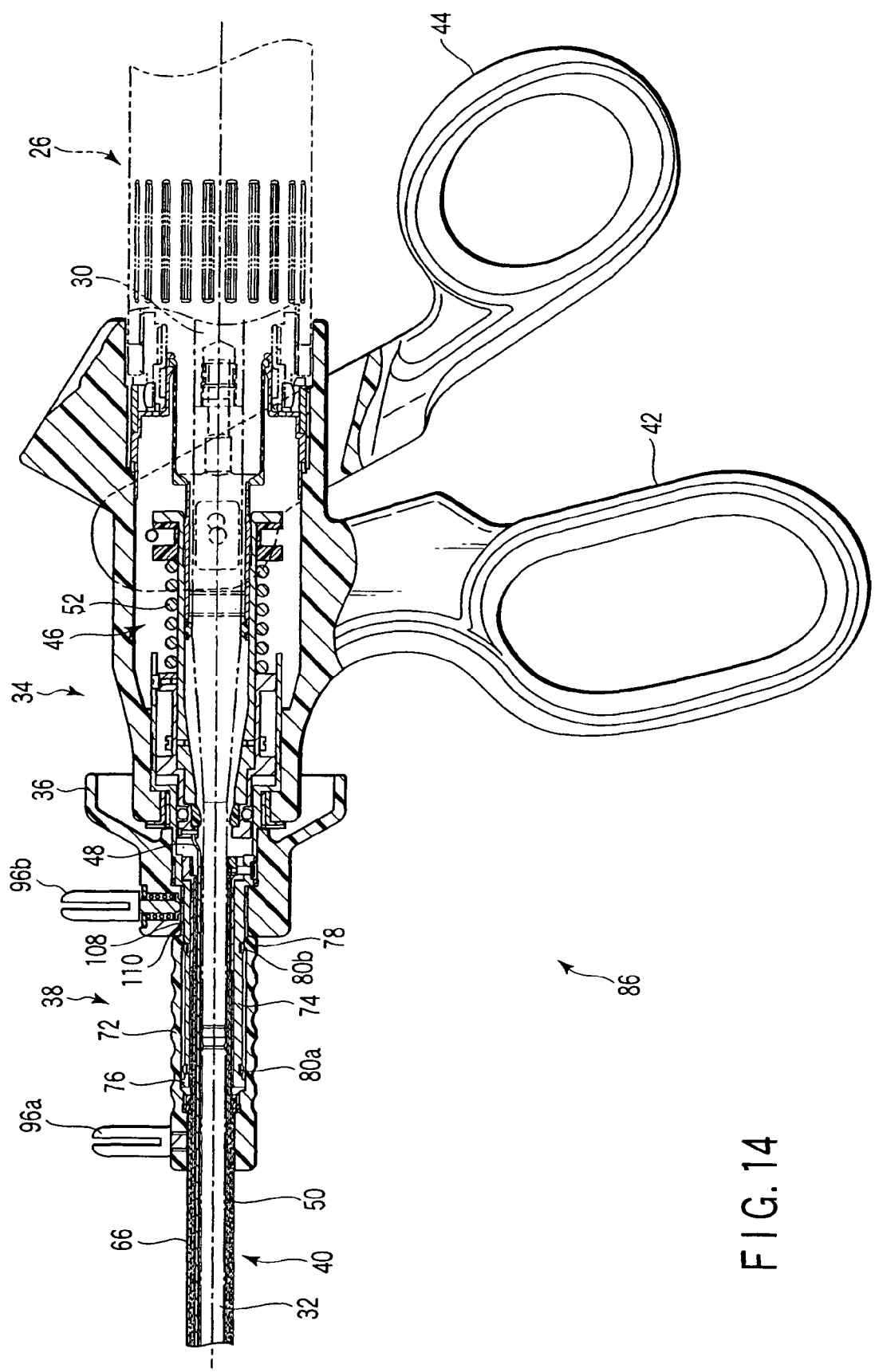
FIG. 14 is a longitudinal sectional view showing a handle unit of the energy accessory in its incision predominant state in the fifth embodiment of the present invention.
Figure 15:
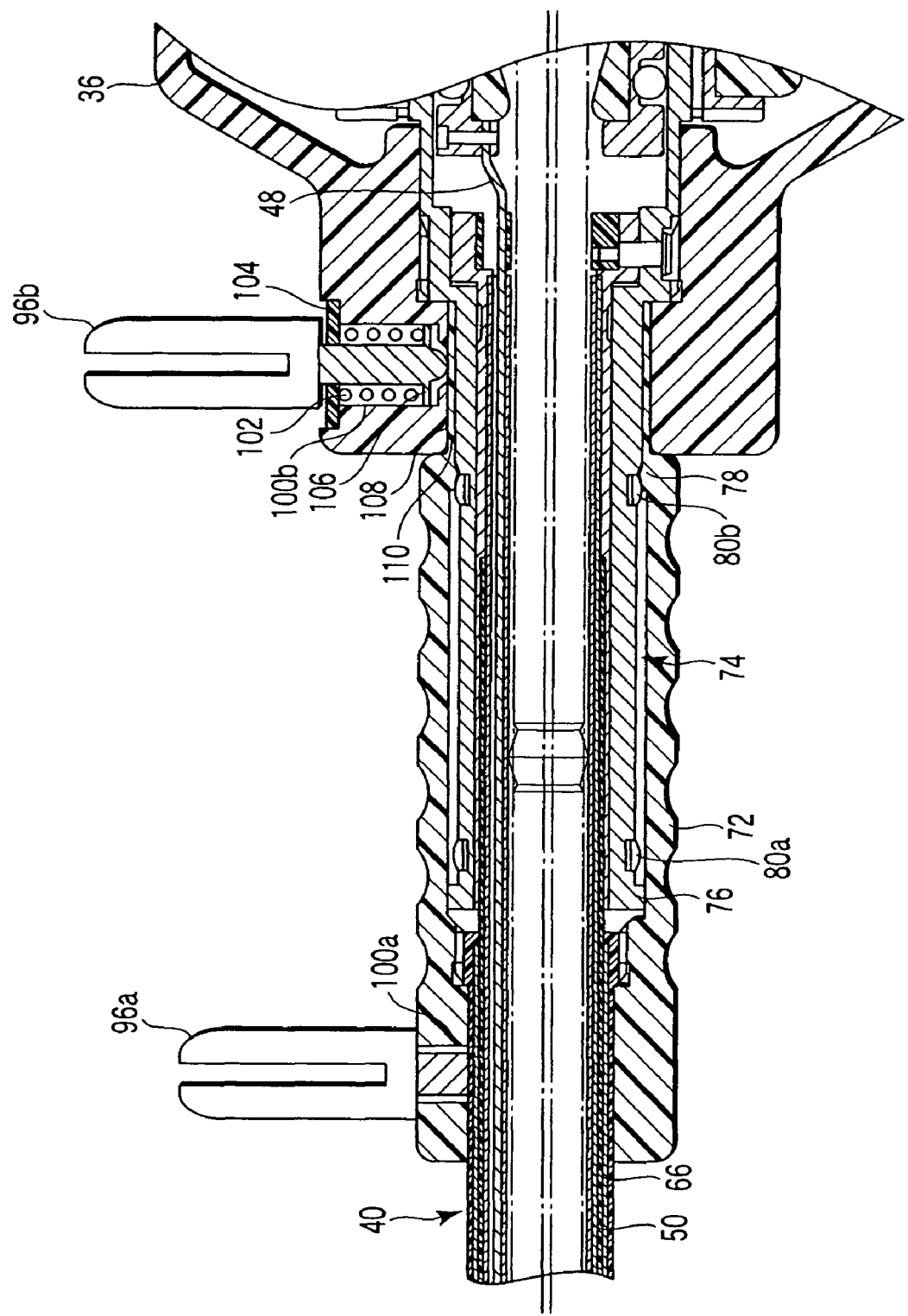
FIG. 15 is a longitudinal sectional view showing a proximal end of an inserting portion of the energy accessory in its incision predominant state in the fifth embodiment of the present invention.

There will be described the energy accessory 86 in the incision predominant state with reference to FIGS. 13 to 16C. As shown in FIGS. 13 to 15, an operation knob 72 is positioned on a proximal end side in a case where the energy accessory 86 is brought into the incision predominant state in the same manner as in the first embodiment. In a distal end portion of the operation knob 72, the first connection terminal 96*a* protrudes in a diametric direction of a central axis of an inserting portion 40. An inner end portion of the first connection terminal 96*a* is inserted through a first through hole 100*a* formed in the operation knob 72 to abut on an outer peripheral surface of a proximal end of an outer tube 66. In the present embodiment, the outer tube 66 is formed by an insulating outer layer and a conductive inner layer, but the outer layer is also conductive in the proximal end of the outer tube 66. Therefore, the inner layer of the outer tube 66 is electrically connected to the inner end portion of the first connection terminal 96*a* which abuts on the outer peripheral surface of the proximal end of the outer tube 66.

On the other hand, the second connection terminal 96*b* is protruded in the diametric direction of the central axis of the inserting portion 40 in the distal end portion of the insulating rotary knob 36. The inner end portion of the second connection terminal 96*b* is inserted through a second through hole 100*b* formed in the rotary knob 36. Moreover, an urging member 102 having a wound spring shape is disposed around the inner end portion of the second connection terminal 96*b*. This urging member 102 is compressed between an insulating cover member 104 which covers the second through hole 100*b* and a flange portion 106 formed on the inner end portion of the second connection terminal 96*b*, and the urging member urges the second connection terminal 96*b* inwards in the diametric direction of the central axis of the inserting portion 40.

Here, the inner end portion of the second through hole 100*b* opens in a clearance between an inner peripheral surface of a rotary knob 36 and an outer peripheral surface of a conductive rotary connecting member 74. A shield receiving portion 108 is formed by this clearance, and an insulating shield portion 110, which is protruded from the proximal end of the operation knob 72 and having a substantially thin cylindrical shape, is fitted into this shield receiving portion 108. Moreover, the proximal end of the second connection terminal 96*b* is allowed to abut on the outer peripheral surface of the shield portion 110 by the urging member 102. That is, in a case where the energy accessory 86 is brought into the incision predominant state in which any high frequency current is not used, the second connection terminal 96*b* is electrically shielded by the insulating rotary knob 36, the insulating cover member 104, and the insulating shield portion 110.

Figure 16A:
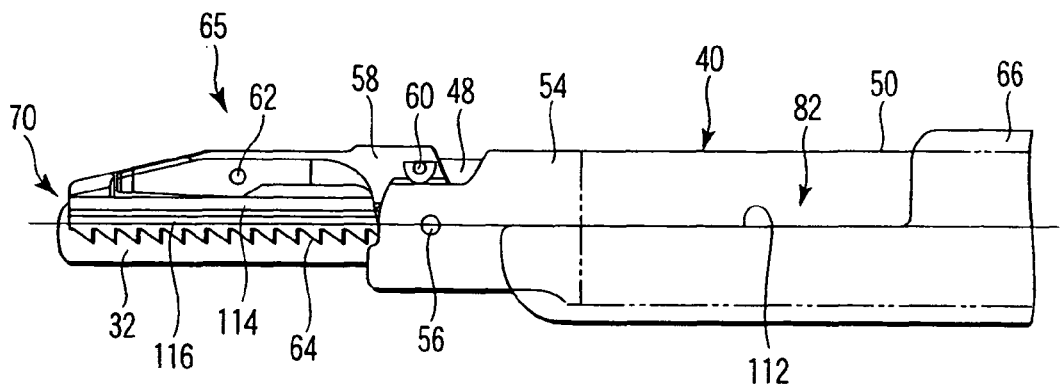
FIG. 16A is a side view showing a distal end portion of the inserting portion of the energy accessory in its incision predominant state in the fifth embodiment of the present invention.
Figure 16B:
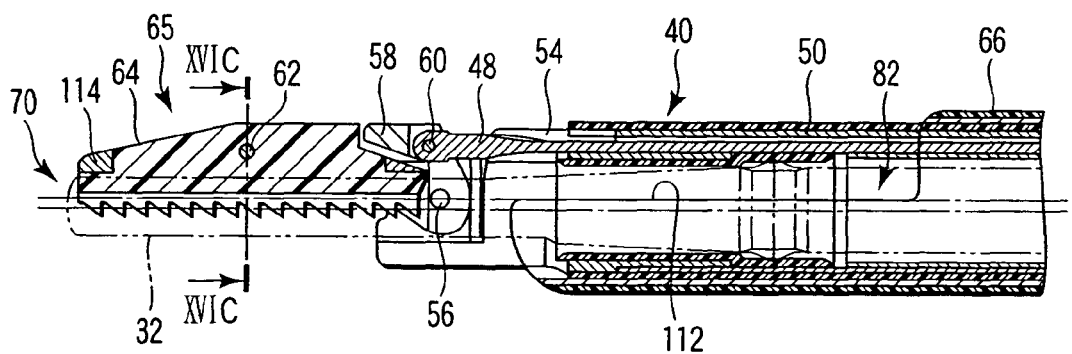
FIG. 16B is a longitudinal sectional view showing the distal end portion of the inserting portion of the energy accessory in its incision predominant state in the fifth embodiment of the present invention.
Figure 16C:
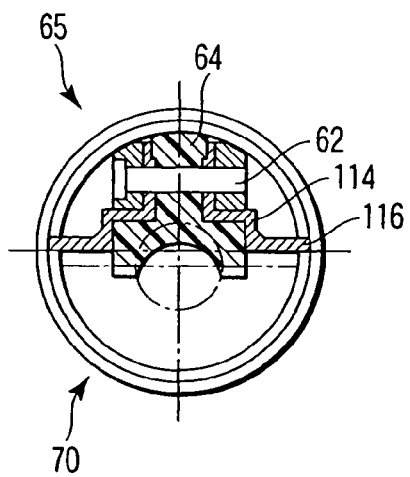
FIG. 16C is a lateral sectional view cut along the line XVIC-XVIC line of FIG. 16B and showing the distal end portion of the inserting portion of the energy accessory in its incision predominant state in the fifth embodiment of the present invention.

It is to be noted that as shown in FIGS. 16A to 16C, a shape of the outer tube 66 is similar to that of the outer tube 66 of the first embodiment. In a case where the energy accessory 86 (see FIG. 13) is brought into the incision predominant state, the distal end portion of the outer tube 66 is disposed on the proximal end side of a clamp portion 70 in the same manner as in the first embodiment.

Figure 17:
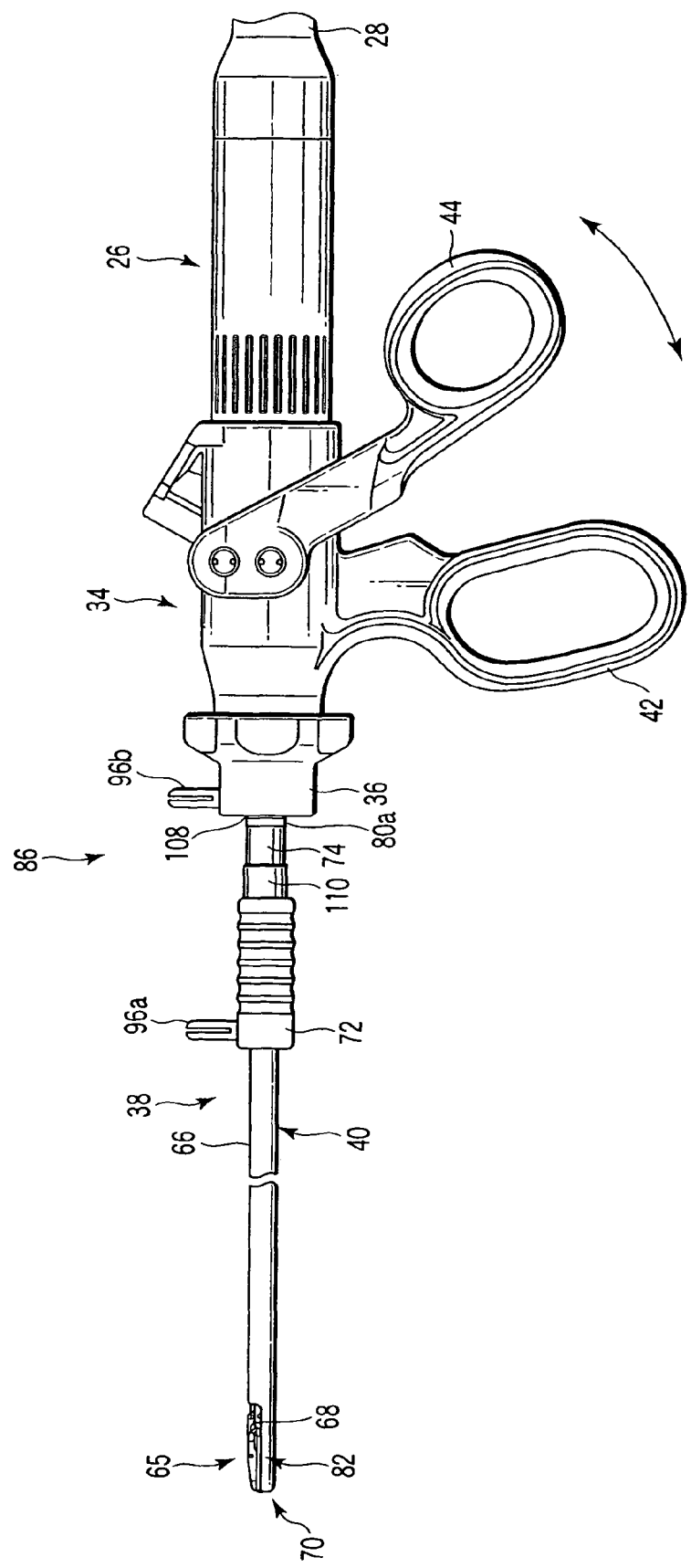
FIG. 17 is a side view showing the energy accessory in its coagulation predominant state in the fifth embodiment of the present invention.
Figure 18:
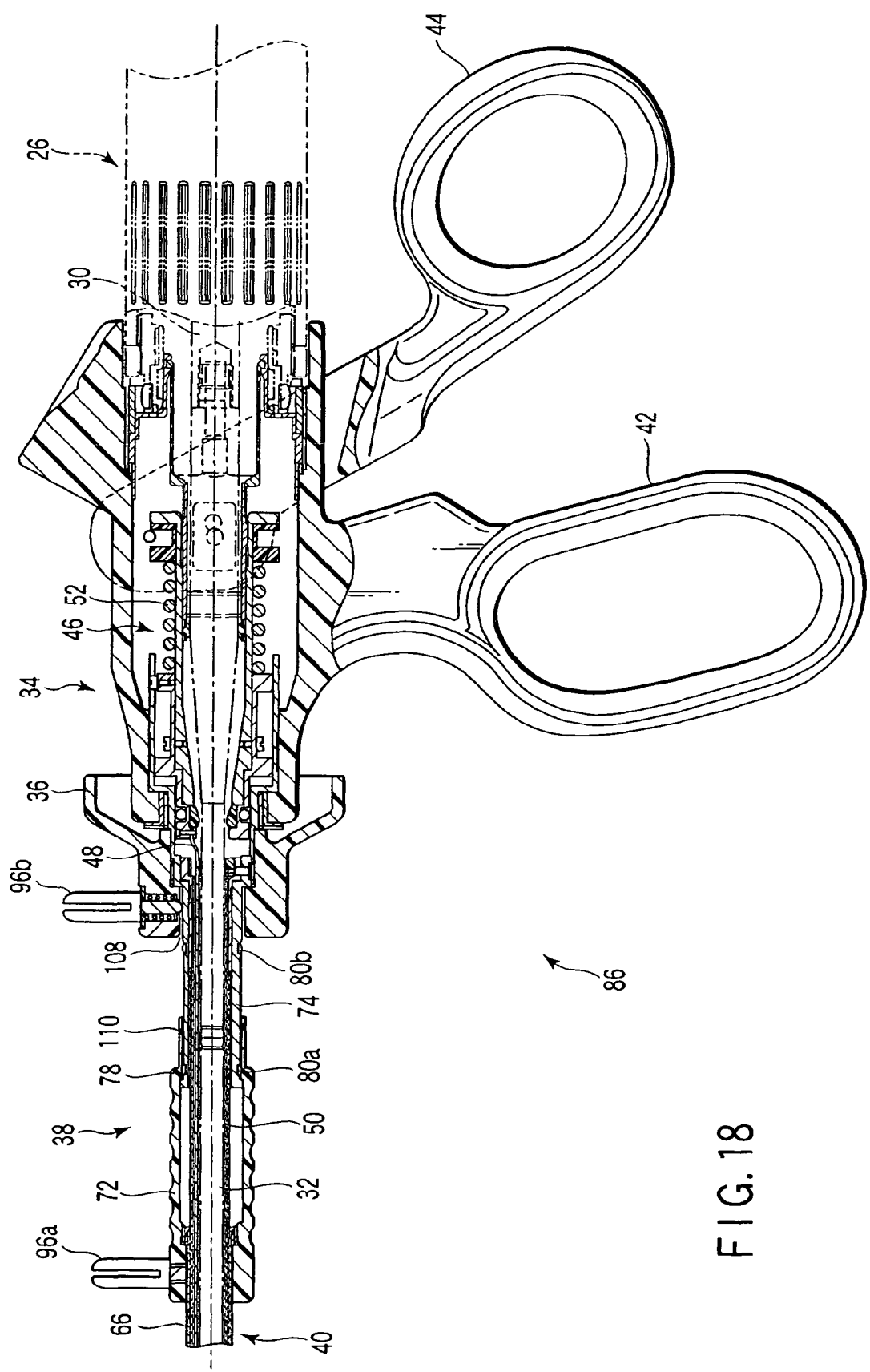
FIG. 18 is a longitudinal sectional view showing the handle unit of the energy accessory in its coagulation predominant state in the fifth embodiment of the present invention.
Figure 19:
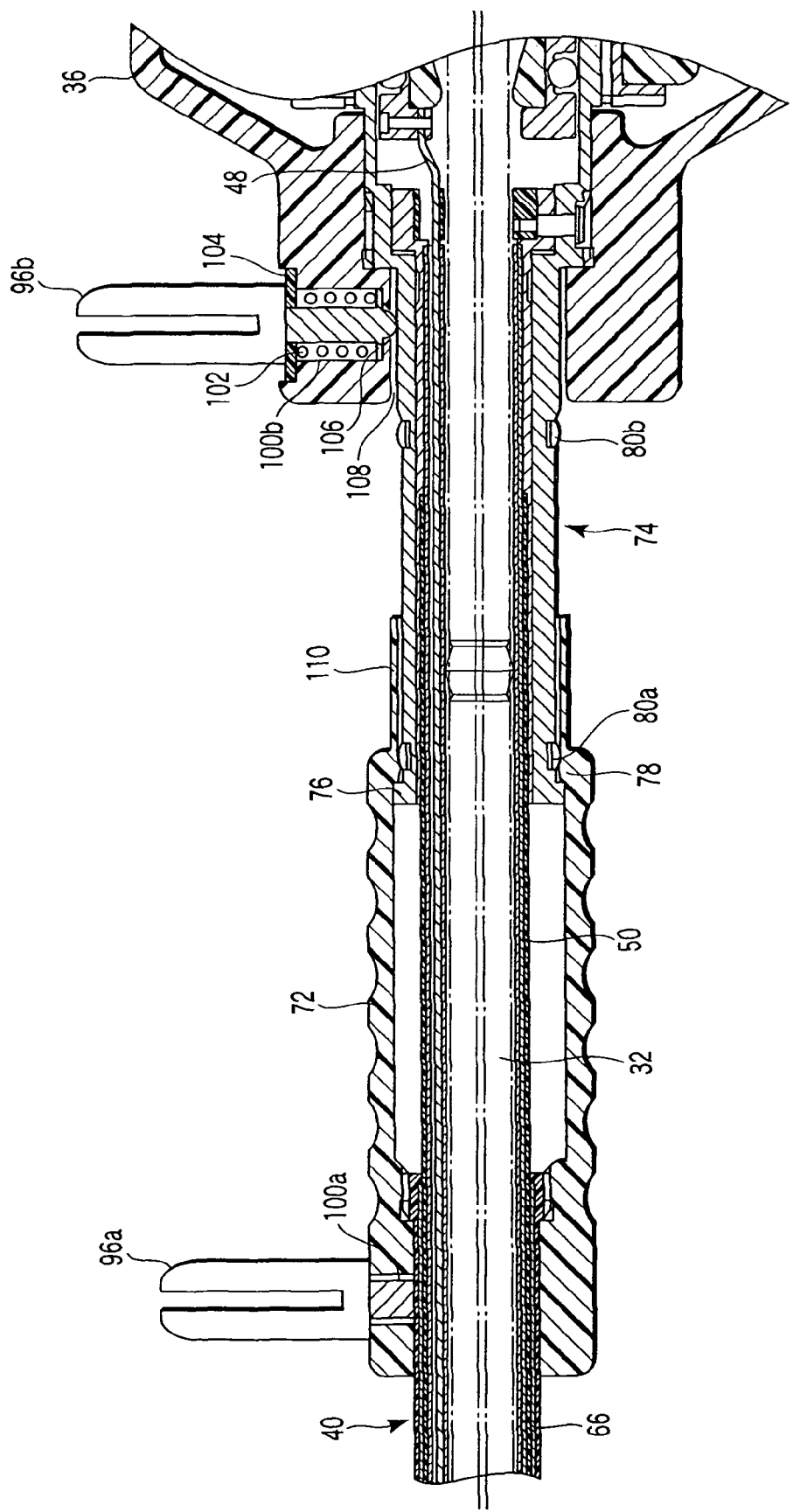
FIG. 19 is a longitudinal sectional view showing the proximal end of the inserting portion of the energy accessory in its coagulation predominant state in the fifth embodiment of the present invention.

There will be described the energy accessory 86 in a coagulating predominant state with reference to FIGS. 17 to 20C. As shown in FIGS. 17 to 19, in a case where the energy accessory 86 is brought into the coagulating predominant state, the operation knob 72 is positioned on the distal end side in the same manner as in the first embodiment. Moreover, the shield portion 110 of the operation knob 72 is removed from the shield receiving portion 108, and the proximal end of the second connection terminal 96b is allowed to abut on the outer peripheral surface of the rotary connecting member 74 by the urging member 102. In the present embodiment, the sheath 50 is formed by an insulating outer layer and a conductive inner layer, the outer layer is also conductive in the proximal end of the sheath 50, and the layer is electrically connected to the rotary connecting member 74. Therefore, the proximal end of the second connection terminal 96b abutted on the outer peripheral surface of the rotary connecting member 74 is electrically connected to the inner layer of the sheath 50.

Figure 20A:
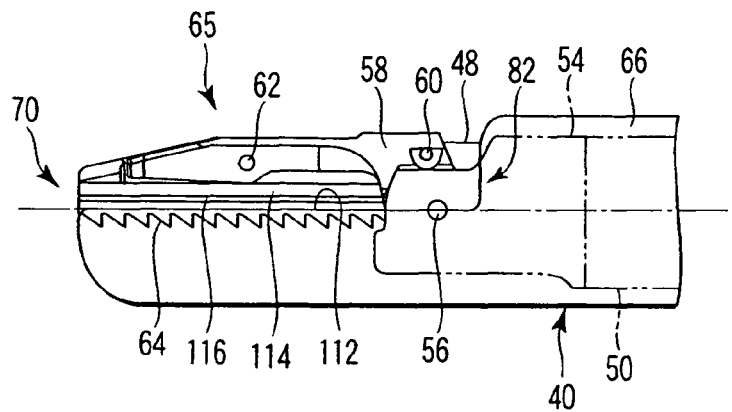
FIG. 20A is a side view showing the distal end portion of the inserting portion of the energy accessory in its coagulation predominant state in the fifth embodiment of the present invention.
Figure 20B:
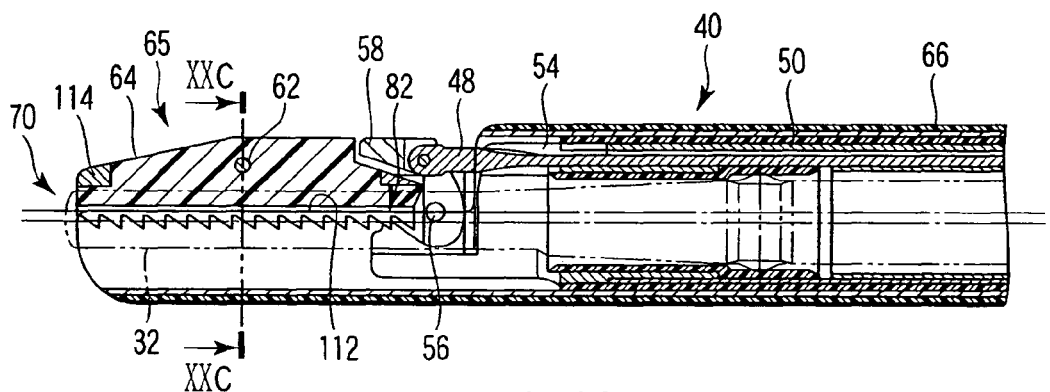
FIG. 20B is a longitudinal sectional view showing the distal end portion of the inserting portion of the energy accessory in its coagulation predominant state in the fifth embodiment of the present invention.

As shown in FIGS. 20A and 20B, in a case where the energy accessory 86 (see FIG. 17) is brought into the coagulating predominant state, the distal end portion of the outer tube 66 as an outer member is disposed in the clamp portion 70 in the same manner as in the first embodiment. In a notch portion 82 of the outer tube 66, an elongated double-face portion is formed which extend in the central-axis direction of the inserting portion 40 on opposite sides of the probe 32. In this double-face portion, there is exposed the inner layer of the outer tube 66 electrically connected to the first connection terminal 96a (see FIG. 19), whereby forming a holding electrode portion 112.

Figure 20C:
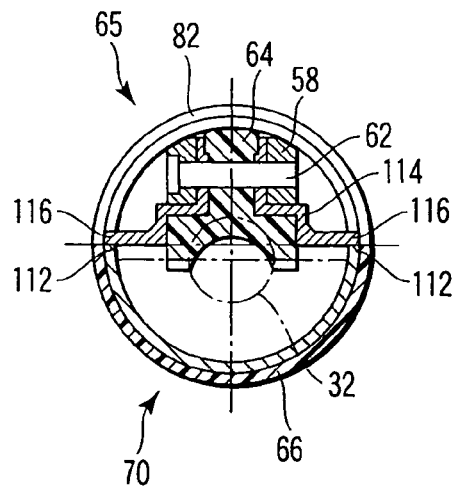
FIG. 20C is a lateral sectional view cut along the line XXC-XXC line of FIG. 20B and showing the distal end portion of the inserting portion of the energy accessory in its coagulation predominant state in the fifth embodiment of the present invention.

On the other hand, the inner layer of the sheath 50 electrically connected to the second connection terminal 96b (see FIG. 19) is electrically connected to a jaw 58 via a jaw holding portion 54 and a holding pin 56. Referring to FIG. 20C, a high frequency grasping member 114 is disposed in the jaw 58, and an ultrasonic grasping member 64 is disposed in the high frequency grasping member 114. The jaw 58, the high frequency grasping member 114, and the ultrasonic grasping member 64 are mutually supported by a seesaw pin 62. The jaw 58 is electrically connected to the high frequency grasping member 114 via the seesaw pin 62, and the second connection terminal 96b (see FIG. 19) is electrically connected to the high frequency grasping member 114. This high frequency grasping member 114 protrudes on opposite sides, and rotary electrode portions 116 are formed on opposite-side end portions of the high frequency grasping member 114. A high frequency current is capable of flowing between rotary electrode portions 116 and the holding electrode portion 112. That is, the rotary electrode portion 116 is formed by an elongated double-face portion which faces the holding electrode portion 112 of the outer tube 66 and is extended in the longitudinal direction of the inserting portion 40 on opposite sides of the ultrasonic grasping member 64. When the jaw 58 is closed, the rotary electrode portion 116 abuts on the holding electrode portion 112.

It is to be noted that in the present embodiment, the ultrasonic grasping member 64 has a constitution substantially similar to that of the grasping member 64 of the first embodiment, but the member does not protrude toward the opposite sides. The member is disposed in the center of the grasping portion 65, and is incapable of coming into contact with the outer tube 66.

As described above, in the present embodiment, the operation knob 72 and the outer tube 66 form a movement mechanism which moves the holding electrode portion 112 between a grasping position wherein the holding electrode portion 112 and the rotary electrode portion 116 is capable of grasping living tissue and a non-grasping position wherein they are incapable of grasping the tissue. The second connection terminal 96b, the urging member 102, and the operation knob 72 form an interrupting mechanism which automatically prevent a current from flowing between the holding electrode portion 112 and the rotary electrode portion 116 in a case where the holding electrode portion 112 is disposed in the non-grasping position.

Next, there will be described an operation of the energy accessory 86 of the present embodiment. There will be described hereinafter a case where a thick blood vessel is incised as an example. In a case where the thick blood vessel is incised, opposite-side regions of a target region to be incised crossing the blood vessel are coagulated beforehand. That is, the operation knob 72 is positioned on the distal end side, and the energy accessory 86 is switched to the coagulating predominant state. In this case, the outer tube 66 is moved toward the distal end side, and the holding electrode portion 112 on the distal end portion of the outer tube 66 is allowed to face the rotary electrode portion 116. The shield portion 110 of the operation knob 72 is removed from the shield receiving portion 108 to electrically connect the second connection terminal 96b to the rotary connecting member 74, and a high frequency current can flow between the holding electrode portion 112 and the rotary electrode portion 116.

The movable handle 44 is opened and closed with respect to the fixed handle 42, and the rotary electrode portion 116 of the high frequency grasping member 114 is opened and closed with respect to the holding electrode portion 112 of the outer tube 66. Target regions to be coagulated on the opposite sides of the target region to be incised are grasped crossing the blood vessel by the holding electrode portion 112 and the rotary electrode portion 116. In this case, the target region to be incised is grasped by the probe 32 and the ultrasonic grasping member 64 with a comparatively small grasping force. Moreover, the high frequency foot switch 92b is operated to operate the electric knife main body 94, and the target region to be coagulated grasped by the holding electrode portion 112 and the rotary electrode portion 116 is subjected to a bipolar high frequency coagulating treatment which is a coagulation predominant treatment. In the present embodiment, two coagulated regions are formed which cross the blood vessel and which are extended parallel to each other depending on shapes of the holding electrode portion 112 and the rotary electrode portion 116.

Thereafter, the blood vessel is incised. That is, the operation knob 72 is positioned on the proximal end side, and the energy accessory 86 is switched to the incision predominant state. In this case, the outer tube 66 is moved to the proximal end side, and the holding electrode portion 112 on the distal end portion of the outer tube 66 is retreated on the proximal end side of the clamp portion 70. The shield portion 110 of the operation knob 72 is fitted into the shield receiving portion 108, and the second connection terminal 96b and the rotary connecting member 74 are electrically insulated.

As described above, in a case where the target region to be coagulated is grasped, since the target region to be incised is already grasped by the probe 32 and the ultrasonic grasping member 64, the target region to be incised does not have to be grasped anew. The ultrasonic foot switch 92a is operated to operate the ultrasonic coagulating and incising device main body 90, and the blood vessel is subjected to the ultrasonic coagulating and incising treatment which is an incision predominant treatment.

Therefore, the energy accessory 86 of the present embodiment produces the following effect. In the present embodiment, the energy accessory 86 is switched to the incision predominant state in which the treatment is performed using the ultrasonic vibration, and the living tissue is subjected to the coagulating and incising treatment which is the incision predominant treatment. On the other hand, the energy accessory 86 is switched to a coagulating predominant state in which the treatment is performed using the high frequency current, and the living tissue is subjected to the coagulating treatment which is a coagulation predominant treatment. Therefore, a coagulating capability and an incising capability can be adjusted in the integral energy accessory 86, and operation efficiency is increased.

Moreover, the operation knob 72 and the outer tube 66 are slid in the axial direction of the longitudinal axis of the inserting portion 40. Whereby, the holding electrode portion 112 is moved to the non-grasping position, the living tissue is grasped by the ultrasonic grasping member 64 and the probe 32, and the ultrasonic vibration is applied to the grasped living tissue to perform the incision predominant treatment, while the holding electrode portion 112 is moved to the grasping position, the living tissue is grasped by the rotary electrode portion 116 and the holding electrode portion 112, and the high frequency current is supplied to the grasped living tissue to perform the coagulation predominant treatment. The energy accessory 86 can be switched between the coagulating predominant state and the incision predominant state with a simple operation in this manner, and the operation efficiency is further improved.

Furthermore, in a case where the holding electrode portion 112 is moved to the non-grasping position, the shield portion 110 of the operation knob 72 is fitted into the shield receiving portion 108 to electrically interrupt the second connection terminal 96b and the rotary connecting member 74, whereby preventing automatically a current from flowing between the holding electrode portion 112 and the rotary electrode portion 116. Therefore, in a case where the energy accessory 86 is brought into the incision predominant state, an unnecessary high frequency current is prevented from flowing between the holding electrode portion 112 and the rotary electrode portion 116 by an erroneous operation of the foot switch 92 or the like.

Figure 22A:
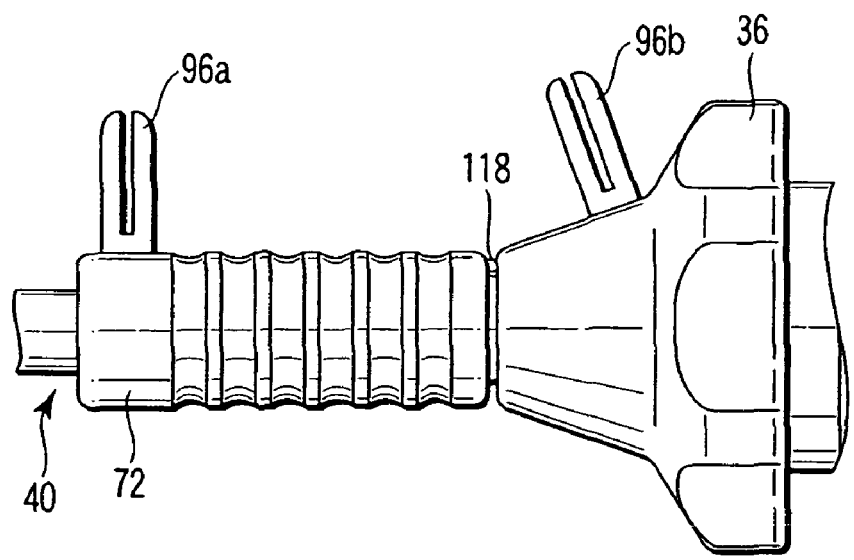
FIG. 22A is a side view showing a proximal end of an inserting portion of an energy accessory in its incision predominant state in the sixth embodiment of the present invention.
Figure 22B:
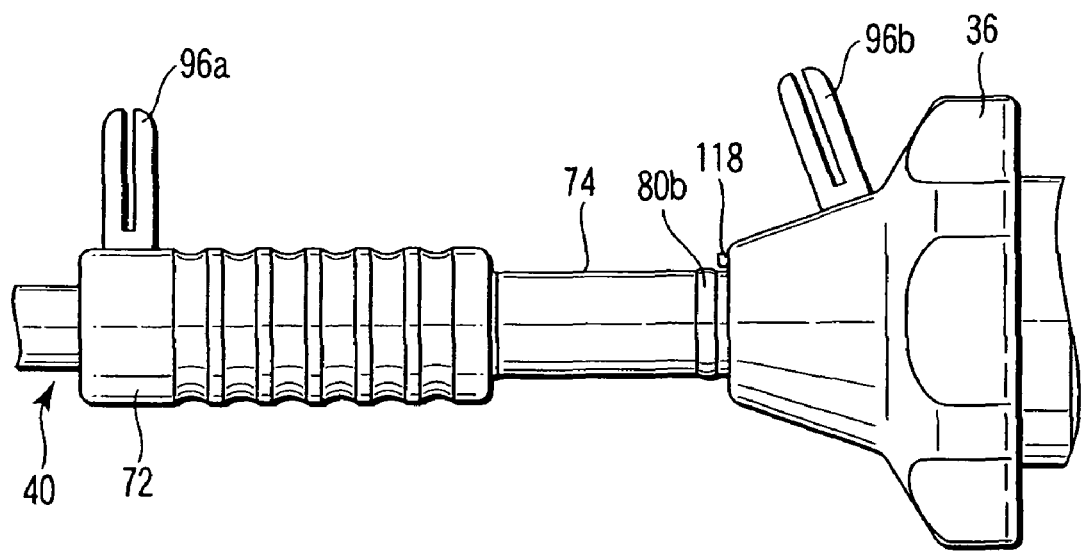
FIG. 22B is a side view showing the proximal end of the inserting portion of the energy accessory in its coagulation predominant state in the sixth embodiment of the present invention.

FIGS. 21 to 22B show a sixth embodiment of the present invention. A constitution having a function similar to that of the fifth embodiment is denoted with the same reference numerous, and description thereof is omitted. In the present embodiment, an ultrasonic coagulating and incising device main body 90 and an electric knife main body 94 are operated by a single foot switch 92.

In FIG. 21, an input to the foot switch 92 is transmitted to both of the ultrasonic coagulating and incising device main body 90 and the electric knife main body 94 by radio communication, and both of the ultrasonic coagulating and incising device main body 90 and the electric knife main body 94 can be operated by the foot switch 92.

Moreover, as shown in FIGS. 21 to 22B, a distal face of a rotary knob 36 is provided with a changeover switch 118 capable of being protruded and depressed. Moreover, in a case where an operation knob 72 is positioned in a proximal end side fixing position, a holding electrode portion 112 is disposed in a non-grasping position in the same manner as in the fifth embodiment, and the changeover switch 118 is turned on by the proximal end of the operation knob 72. When the changeover switch 118 is turned on, an operation signal is output to the ultrasonic coagulating and incising device main body 90 via a hand piece cord 28, and the ultrasonic coagulating and incising device main body 90 becomes operable. Moreover, a stop signal is output to the electric knife main body 94 via a second connection terminal 96b, and an operation of the electric knife main body 94 is stopped. This is an incision predominant state of an energy accessory 86.

On the other hand, in a case where the operation knob 72 is positioned in a distal end side fixing position, in the same manner as in the fifth embodiment, the holding electrode portion 112 is disposed in a grasping position, the depressed changeover switch 118 by the proximal end of the operation knob 72 is released, and the changeover switch 118 is turned off. When the changeover switch 118 is turned off, the operation signal is output to the electric knife main body 94 via the second connection terminal 96b, and the electric knife main body 94 becomes operable. Moreover, the stop signal is output to the ultrasonic coagulating and incising device main body 90 via the hand piece cord 28, and the operation of the ultrasonic coagulating and incising device main body 90 is stopped. This is a coagulating predominant state of the energy accessory 86.

Next, there will be described an operation of the energy accessory 86 in the present embodiment. In a case where living tissue is subjected to a bipolar high frequency treatment which is a coagulation predominant treatment, the operation knob 72 is positioned in a distal end side fixing position. As a result, the holding electrode portion 112 is disposed in the grasping position, and the only electric knife main body 94 becomes operable. In this state, the foot switch 92 is operated to operate the electric knife main body 94, and the bipolar high frequency treatment is performed on the living tissue. On the other hand, in a case where performed is the ultrasonic coagulating and incising treatment which is an incision predominant treatment on the living tissue, the operation knob 72 is positioned in the proximal end side fixing position. As a result, the holding electrode portion 112 is disposed in the non-grasping position, and the only ultrasonic coagulating and incising device main body 90 becomes operable. In this state, the foot switch 92 is operated to operate the ultrasonic coagulating and incising device main body 90, and the ultrasonic coagulating and incising treatment is performed on the living tissue.

Therefore, in the present embodiment, the energy accessory produces the following effect. In the present embodiment, in a case where both of the ultrasonic coagulating and incising device main body 90 and the electric knife main body 94 are operable by the foot switch 92. In a case where the energy accessory 86 is brought into the incision predominant state, only the ultrasonic coagulating and incising device main body 90 is set to be operable, while in a case where the energy accessory 86 is brought into the coagulating predominant state, only the electric knife main body 94 is set to be operable. In consequence, both of an ultrasonic output and a high frequency output can be operated by the single foot switch 92, and an operation efficiency is improved.

What is claimed is:
1. An energy accessory comprising:
an ultrasonic vibrator configured to generate ultrasonic vibration;
an elongated probe including a proximal end connected to the ultrasonic vibrator and configured to transmit the ultrasonic vibration generated by the ultrasonic vibrator from a proximal end side to a distal end side;
a sheath provided on the proximal end side of the probe;
a jaw provided on a distal end portion of the sheath and configured to be opened and closed with respect to the probe;
a first electrode provided on the jaw;
a shaft provided within the sheath movable in a longitudinal axial direction of the probe with respect to the probe, including a distal end portion connected to the jaw, wherein the shaft is configured to be moved in the longitudinal axial direction to open and close the jaw with respect to the probe;

an outer tube provided on the sheath movable in the longitudinal axial direction of the probe with respect to the probe and including a distal end portion; and a second electrode provided on the distal end portion of the outer tube, configured to be moved between a distal grasping position wherein the second electrode faces the jaw and a proximal non-grasping position wherein the second electrode is arranged closer to the proximal end side than the jaw, by moving the outer tube in the longitudinal axial direction of the probe with respect to the probe, and configured so that a high frequency current is to flow between the first electrode and the second electrode, and wherein the energy accessory is configured to grasp a living tissue by the jaw and the probe to perform a treatment to the living tissue grasped by the jaw and the probe by use of ultrasonic vibration of the probe when the second electrode is positioned in the non-grasping position and configured to grasp a living tissue by the jaw and the second electrode to perform a treatment to the living tissue grasped by the jaw and the second electrode by use of a high frequency current flowing between the first electrode and the second electrode through the living tissue grasped by the jaw and the second electrode when the second electrode is positioned in the grasping position jaw.

2. The energy accessory according to claim 1, further comprising:

an interrupting mechanism configured to prevent automatically a current from flowing between the first electrode portion and the second electrode portion in a case where the second electrode portion is positioned in the non-grasping position.

3. The energy accessory according to claim 1, wherein the jaw includes an ultrasonic grasping part and a high frequency grasping part provided with the first electrode, the ultrasonic grasping part and the probe are configured to grasp a living tissue when the second electrode is positioned in the non-grasping position, and the high frequency grasping part and the second electrode are configured to grasp a living tissue when the second electrode is positioned in the grasping position.

4. The energy accessory according to claim 3, wherein the first electrode is attached to the jaw and arranged on both sides of the ultrasonic grasping part, and the outer tube includes the second electrode arranged on both sides of the probe when the second electrode is positioned in the grasping position.

5. The energy accessory according to claim 2, wherein the interrupting mechanism including a first and a second electric connecting member, and an urging member configured to urge the first electric connecting member toward the second electric connecting member, and an interrupting portion provided on the outer tube, wherein the interrupting portion is configured to be put out between the first electric connecting member and the second electric connecting member by the outer tube wherein the first electric connecting member is to be brought into contact with the second electric connecting member due to the urging by the urging member to enable a high frequency current to flow to the first and the second electrode through the first and second electric connecting member when the second electrode is positioned in the grasping position, and configured to be put between the first electric connecting member and the second electric connecting member by the outer tube wherein the interrupting portion is to disable a high frequency current to flow to the first and the second electrode through the first and the second electric connecting member when the second electrode is positioned in the non-grasping position.

* * * * *